(12) United States Patent
Wu

(10) Patent No.: US 11,377,499 B2
(45) Date of Patent: Jul. 5, 2022

(54) TARGETING THE COFILIN PATHWAY

(71) Applicant: George Mason University, Fairfax, VA (US)

(72) Inventor: Yuntao Wu, Manassas, VA (US)

(73) Assignee: George Mason University, Fairfax, VA (US)

( * ) Notice: Subject to any disclaimer, the term of this patent is extended or adjusted under 35 U.S.C. 154(b) by 0 days.

(21) Appl. No.: 16/201,695

(22) Filed: Nov. 27, 2018

(65) Prior Publication Data

US 2019/0169297 A1    Jun. 6, 2019

Related U.S. Application Data

(60) Provisional application No. 62/593,335, filed on Dec. 1, 2017.

(51) Int. Cl.

| C07K 16/28 | (2006.01) |
| A61P 31/18 | (2006.01) |
| A61K 39/395 | (2006.01) |
| C12N 5/0783 | (2010.01) |
| G01N 33/50 | (2006.01) |
| A61K 45/06 | (2006.01) |
| A61K 39/00 | (2006.01) |

(52) U.S. Cl.
CPC ...... *C07K 16/2839* (2013.01); *A61K 39/3955* (2013.01); *A61P 31/18* (2018.01); *C12N 5/0636* (2013.01); *G01N 33/505* (2013.01); *A61K 45/06* (2013.01); *A61K 2039/505* (2013.01); *C07K 2317/21* (2013.01); *C07K 2317/24* (2013.01); *C12N 2501/998* (2013.01)

(58) Field of Classification Search
None
See application file for complete search history.

(56) References Cited

PUBLICATIONS

Byrareddy et al. (Science, Oct. 2016, vol. 354, p. 197-202).*
Wu et al. (Retroviroly, 2008, p. 1-6).*
Madrazo et al. (Cancers, Jul. 2017, p. 1-17).*
Byrareddy et al., "Sustained virologic control in SIV+ macaques after antiretroviral and alpha4beta7 antibody therapy," Oct. 2016. Science, 354(6309): 197-203.
Cecchinato et al., "Impairment of CCR6+ and CXCR3+ Th Cell Migration in HIV-1 Infection is Rescued by Modulating Actin Polymerization," Nov. 2016. Journal of Immunology, v. 198, 13 pages.
He et al., "Cofilin hyperactivation in HIV infection and targeting the cofilin pathway using an anti-alpha4beta7 integrin antibody," Jan. 2019. Science Advances, 5:eaat7911. 12 pages.
Shen et al., "Inside-out, outside-in, and inside-outside-in: G protein signaling in integrin-mediated cell adhesion, spreading, and retraction," Oct. 2012. Curr Opin Cell Biol, 24(5): 600-606.
Spear et al., "Novel anti-HIV therapeutics targeting chemokine receptors and actin regulatory pathways," 2013. Immunological Reviews, 256:300-312.
Vorster et al., "LIM kinase 1 modulates cortical actin and CXCR4 cycling and is activated by HIV-1 to initiate viral infection," Apr. 2011. Journal of Biological Chemistry, 286(14): 12554-12564.
Wu and Yoder, "Chemokine coreceptor signaling in HIV-1 infection and pathogenesis," Dec. 2009. PLoS Pathogens, 5(12): e10000520. 8 pages.
Wu et al., "Cofilin activiation in peripheral CD4 T cells of HIV-1 infected patients: a pilot study," Oct. 2008. Retrovirology, 5:95. 6 pages.
Yi et al., "Discovery of novel small-molecule inhibitors of LIM domain kinase for inhibiting HIV-1," Apr. 2017. Journal of Virology, 13(91): e02418-16. 21 pages.
Yoder et al., "HIV envelope-CXCR4 signaling activates cofilin to overcome cortical actin restriction in resting CD4 T cells," Sep. 2008. Cell. 134: 782-792.

* cited by examiner

*Primary Examiner* — Agnieszka Boesen
(74) *Attorney, Agent, or Firm* — Dave Law Group LLC; Raj S. Dave

(57) ABSTRACT

The present disclosure provides a method of restoring immune reconstitution, immune control of viremia, and one or more T cell functions in a subject infected with HIV. The method includes administering to the subject infected with HIV an agent that targets the cofilin pathway.

19 Claims, 8 Drawing Sheets

5A

5B

TARGETING THE COFILIN PATHWAY

CROSS REFERENCE TO RELATED PATENT APPLICATIONS

This application claims the benefit of U.S. Provisional Patent Application No. 62/593,335, filed on Dec. 1, 2017, which is hereby incorporated by reference in its entirety

TECHNICAL FIELD

The present disclosure discloses methods of treating AIDS.

BACKGROUND

Acquired immunodeficiency syndrome (AIDS) is caused by the human immunodeficiency virus (HIV), a lentivirus, which causes progressive failure of the immune system and leads to life-threatening opportunistic infections and cancers. AIDS is a sexually transmitted infection that occurs by contact with or transfer of bodily fluids including blood, semen, and vaginal fluids. Non-sexual transmission of AIDS can also occur, for example, transmission by a mother infected with HIV to her infant during pregnancy or during childbirth by exposure of her blood or vaginal fluid and through breast milk.

Treatment of HIV infection usually involves antiretroviral therapy (ART), which involves taking a combination of drugs to slow the progression of the virus in the patient's body. ART reduces the amount of virus (or viral load) in the patient's blood and body fluids to keep a patient's immune system as healthy as possible, ART is usually taken as a combination of three or more drugs to have the greatest chance of lowering the amount of HIV in the patient's body. Over the years, the FDA has approved several nucleoside reverse transcriptase inhibitors (NRTI) for treating AIDS. Examples of such drugs include Combivir (Zidovudine and Lamivudine), Trizivir (Zidovudine, Lamivudine and Abacavir), Epzicom (Abacavir and Lamivudine) and Truvada (Tenofovir and Lamivudine).

Although ART has significantly extended the lifespan of HIV-infected patients, it does not cure AIDS, nor does it provide complete immune restoration to the patient. Accordingly, there is a need to develop new and improved drugs to achieve immune control of viremia.

SUMMARY

The present disclosure describes methods of targeting the cofilin pathway to restore T cell motility, T cell tissue repopulation, and/or T cell migration and homing to lymphoid and non-lymphoid tissues. In embodiments, the T cell motility, T cell tissue repopulation, and/or T cell migration and homing to lymphoid and non-lymphoid tissues are impaired as a result of an HIV infection. The present disclosure also describes methods of targeting the cofilin pathway to promote CD4 T cell repopulation and/or to reverse hyperactivation of cofilin in response to an HIV infection. Moreover, the present disclosure describes methods of promoting immune reconstitution and/or immune control of viremia by targeting the cofilin pathway. Further, the present disclosure provides methods of treating AIDS and/or alleviating the symptoms caused by an HIV infection in a subject.

The methods described herein include using an agent that targets the cofilin pathway. The agent can be a protein that binds the α4β7 integrin. In embodiments, the protein is an antibody, and the antibody is the α4β7 integrin antibody.

The methods described herein also include methods of screening for drugs for treating AIDS and/or alleviating the symptoms caused by an HIV infection in a subject.

DETAILED DESCRIPTION

Figure 1:
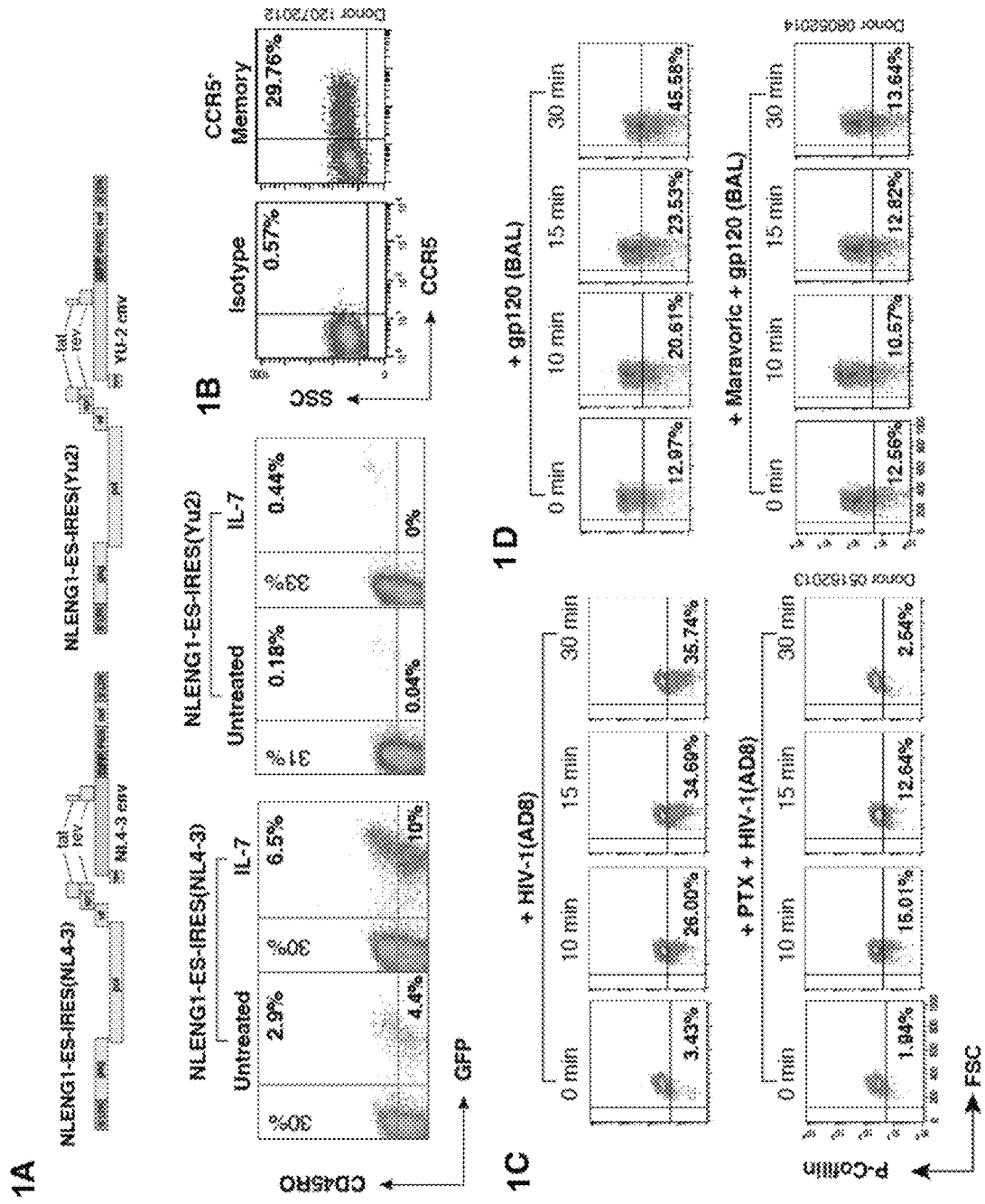
FIGS. 1A-1D show HIV gp120-CCR5 signaling activates cofilin in memory CD4 T cells. (A) Blood resting CD4 T cells were infected with GFP reporter HIV-1 pseudo-typed with NL4-3 (X4) or Yu-2 (R5) envelope. Cells were infected for 6 days with or without IL-7, and analyzed for CD45RO and GFP expression. (B) Resting memory CD4 T cells were stained for surface CCR5 expression. (C) Resting memory CD4 T cells were infected with HIV-1(AD8) in the presence or absence of PTX. Cofilin phosphorylation was measured by intracellular staining and flow cytometry. (D) Resting memory CD4 T cells were treated with gp120(BAL) in the presence or absence of maravoric.

HIV infects the critical cells in the mammalian immune system, such as the helper T cells, specifically the CD4 T cells, macrophages, and dendritic cells. The natural course of HIV infection leads to multiple CD4 T cell defects such as loss of T cell response (2) and T cell anergy (3, 4). These defects are also associated with impairment of T cell migration and homing to lymphoid tissues such as GALT (Gut-Associated Lymphoid Tissues) (5-7). Even with near-complete viral suppression with ART, normal levels of CD4 T cell repopulation to GALT and other lymphoid tissues are rarely achieved (6, 8-11), thereby dampening immune responses and preventing full immune reconstitution. Given that the vast majority of circulating CD4 T cells are not HIV-infected (0.2-16.4 HIV+ cells per million) (12), the T cell migratory defect likely results from a bystander effect from chronic signaling by viral (13, 14) and/or inflammatory factors (5). However, no key intracellular molecule representing HIV-mediated CD4 T cell dysfunction has yet been recognized. This has hindered the identification of effective therapeutic targets to restore T cell functions and to achieve immune control of viremia.

The present disclosure describes cofilin as a key molecule that needs to be therapeutically targeted for T cell tissue repopulation, immune reconstitution, and immune control of viremia. The present disclosure shows that blood CD4 T cells from HIV-infected patients (n=193), with or without antiretroviral therapy (ART), exhibit significantly higher levels of cofilin dephosphorylation (hyperactivation) than those from healthy controls (n=100) (ratio=1.1/2.3; p<0.001). These results suggest a systemic cofilin-mediated T cell migratory defect that cannot be reversed solely by ART. The present disclosure further demonstrates that at low dosages, an anti-human-α4β7 method of regulating T cell motility by targeting the cofilin pathway.

Cell migration requires the processes of rapid changes in the dynamics of actin filaments and the formation and the disassembly of cell adhesion sites acting in a coordinated manner. Cofilin regulates actin dynamics for cell motility. Cofilin phosphorylation by LIM kinase renders it incapable of depolymerization activity, and cofilin dephosphorylation or hyperactivation can cause insufficient actin polymerization, which impairs T cell migration and homing to lymphoid and non-lymphoid tissues. Cofilin belongs to the actin-depolymerizing factor (ADF)/cofilin family of actin-binding proteins. In mammals, there are three forms of ADF/cofilin proteins. The major ubiquitous form in mammalians is cofilin-1, which has been studied extensively. As used herein, the terms "cofilin-1" and "cofilin" refer to the same protein. Other names for cofilin includes CFL-1, CFL, and Hel-S-15. In embodiments, the cofilin used in the methods described herein is cofilin-1, and the cofilin is involved in cell motility including lymphocyte motility, for example the migration and homing of CD4 T cells.

Lymphocytes are white blood cells. Examples of lymphocytes include T cells, B cells, and natural killer cells. T cells are a type of lymphocyte that plays a central role in cell-mediated immunity. In contrast to other lymphocytes, T cells include a T-cell receptor on their cell surface. T cells, as the name suggests, mature in the thymus from thymocytes. Some also mature in the tonsil. There are several subsets of T cells, and each has a distinct function. Examples of T cells include helper T cells, effector T cells, cytotoxic T cells, regulatory T cells, and memory T cells.

In embodiments, the T cells are helper T cells ($T_H$ cells) that assist other white blood cells in processes such as maturation of B cells into plasma cells and memory B cells, and activation of cytotoxic T cells and macrophages. In embodiments, the $T_H$ cells are CD4 T cells, which express the CD4 glycoprotein on their surface. CD4 T cells are activated when they are presented with peptide antigens by MHC class II molecules expressed on the surface of antigen-presenting cells (APCs). Upon activation, CD4 T cells differentiate into specific subtypes, including $T_H1$, $T_H2$, $T_H3$, $T_H17$, $T_H9$, or $T_{FH}$, which secrete different cytokines to facilitate different types of immune responses.

T cells need to move and get to the site to orchestrate a response. Thus, T cell motility is essential for T cell responses, allowing for detection of cognate antigen at the surface of an antigen presenting cell (APC) and for interactions with other cells involved in the immune response. T cell migration and homing is the phenomenon whereby cells migrate to the organ or tissue for performing their role. As an example, the homing of CD4 T cells into the gut was previously reported to be mediated by CCR6, which acts as a marker for these cells to become HIV targets and promote persistence.

The present disclosure describes methods of using agents that target the cofilin pathway for regulating T cell functions, including restoring and/or promoting T cell migration and homing. The agents used in the methods described herein include: small molecules agonists or antagonists of chemotactic receptors, such as chemokine receptors, integrin receptors, or other receptors activating the actin/cofilin pathway; antibodies, such as antibodies stimulating chemokine or integrin receptors such as anti-CXCR4, anti-CCR5, or Act-1; small molecule protein inhibitors or activators of G proteins and GTPases; small molecule protein inhibitors or activators of cofilin regulators (the upstream cofilin pathway regulators such as Rac1. PAK1/2, LIMK1/2 et al); cofilin kinase (LIMK kinase) activators and inhibitors; and cofilin phosphatase (slingshot) inhibitors or activators.

Integrins are transmembrane receptors involved in signal transduction pathways that mediate cellular signals such as regulation of the cell cycle, organization of the intracellular cytoskeleton, and movement of new receptors to the cell membrane. Integrins facilitate cell-extracellular matrix (ECM) adhesion, and upon binding to ligands, integrins activate the signal transduction pathways. Integrins are also involved in other cellular processes including cell migration. As an example, immunodeficiency disorders have been associated with altered integrin-mediated adhesion and migration.

Cell migration is controlled by external stimuli that are transduced into intracellular biochemical signals through the binding of transmembrane integrins with the extracellular matrix proteins. Integrins mediate dynamic interactions between the extracellular matrix and the actin cytoskeleton during cell motility. Integrins have a large extracellular domain that binds the extracellular matrix protein and links to the actin cytoskeleton through a short cytoplasmic tail. Integrins bind to specific motifs within the matrix protein, such as the RGD motif (Arg-Gly-Asp).

Structurally, integrins are heterodimeric cell surface adhesion receptors composed of an alpha subunit and a beta subunit. There are 24 different heterodimers formed by the association of 18 alpha and 8 beta subunits. Various combinations of the alpha chain and beta chain form different integrins.

As an example, CD49d (ITGA4) is an integrin alpha subunit which pairs with ITGB7 (integrin 67), an integrin beta subunit, to form a heterodimeric integrin α4β7 (LPAM). The α4β7 integrin is expressed on lymphocytes and has been shown to be responsible for T cell homing into gut associated lymphoid tissues lymphoid tissues through its binding to mucosal addressin cell adhesion molecule (MAdCAM), which is present on high endothelial venules of mucosal lymphoid organs.

The present disclosure describes agents that target the cofilin pathway to affect migration and homing of T cells. Agents that target the cofilin pathway can be agonists and antagonists that regulate or modulate the cofilin pathway. The agent regulates or modulates the cofilin pathway by up-regulating or down-regulating the activity of the pathway. In embodiments, the agent regulates the cofilin pathway by deactivating or reversing hyperactivation of cofilin to provide adequate polymerization of actin. The agent can be a protein or a small molecule that binds a molecule of the cofilin pathway with certain specificity and/or affinity, for example with an affinity ($K_D$ (M)) of at least about $10^{-6}$, at least about $10^{-7}$, at least about $10^{-8}$, or at least about $10^{-9}$ or more.

Such agents include agents that binds the α4β7 integrin. In embodiments, the agent is a protein, for example, an α4β7 integrin antibody or a biologically functional fragment thereof. The antibody or fragment thereof has a binding specificity for a mammalian α4β7 integrin, such as a human α4β7 integrin. In embodiments, the antibody binds the mammalian α4β7 integrin with an affinity ($K_D$ (M)) of at least about $10^{-6}$, least about $10^{-7}$, at least about $10^{-8}$, or at least about $10^{-9}$ or more.

The present disclosure describes one or more α4β7 integrin antibodies or one or more fragments thereof for targeting the cofilin pathway to affect migration and homing of T cells. The α4β7 integrin antibody can be a monoclonal antibody, a polyclonal antibody, a humanized antibody, a human antibody, a chimeric antibody, and biologically functional fragments thereof. Examples of α4β7 integrin antibodies include mouse and rat monoclonal LPAM-1 antibody, rabbit polyclonal LPAM-1 antibody, and vedolizumab. Vedolizumab (brand name Entyvio), also known as MLN-02, LDP-02, MLN0002, is a humanized IgG-1 monoclonal antibody.

Antibodies can be obtained by using an appropriate immunogen in a suitable mammal (e.g., a mouse, rat, rabbit, sheep). Preparation of the immunogen, and the production of the polyclonal and monoclonal antibody can be performed using any known suitable technique, as described by Kohler et al, Nature, 256: 495-497 (1975) and Ewr. J. Immunol. 6: 511-519 (1976); Milstein et al, Nature 266: 550-552 (1977); Koprowski et al, U.S. Pat. No. 4,172,124; Harlow, E. and D. Lane, 1988, Antibodies: A Laboratory Manual, (Cold Spring Harbor Laboratory: Cold Spring Harbor, N.Y.); Current Protocols In Molecular Biology, Vol. 2 (Supplement 27, Summer '94), Ausubel, F. M. et al, Eds., (John Whey & Sons: New York, N.Y.), Chapter 11, (1991)). Suitable immunizing agents include cells bearing α4β7, membrane fractions containing α4β7, immunogenic fragments of suitable immunogens include α4β7, a β7 peptide conjugated to a suitable carrier and the like. Antibody-producing cells, such as a lymphocyte, can be isolated from lymph nodes or spleen of an immunized animal. The cells can then be fused to a suitable immortalized cell, for example, a myeloma cell line (SP2/0, P3x63Ag8.653), thereby forming a hybridoma. Fused cells can be isolated employing selective culturing techniques. Cells which produce antibodies with the desired specificity can be selected using a suitable assay, such as ELISA. Other methods for obtaining the desired antibodies include selecting recombinant antibodies from a phage display library. Moreover, transgenic animals capable of producing human antibodies, such as XenoMouse™ (Abgenix, Fremont, Calif.), can also be used (see WO 98/24893 (Abgenix), U.S. Pat. No. 5,939,598, Jakobovits et al, Proc. Natl. Acad. Sci. USA, 90: 2551-2555 (1993); Jakobovits et al, Nature, 362: 255-258 (1993)).

The terms "biologically functional fragment" or "fragment" of the antibodies or "antigen-binding fragment" are used interchangeably and refer to fragments of the whole antibody that retain at least one antigen binding function of the full length antibody. In embodiments, the fragments of the antibodies are fragments of the α4β7 integrin antibodies. Such fragments have the ability to bind α4β7 integrin and target the cofilin pathway. Examples of biologically functional fragments of the α4β7 integrin antibodies that can be used in the methods described herein include fragments capable of binding to an α4β7 integrin, for example single chain antibodies, Fv, Fab, Fab' and F(ab')$_2$ fragments. Such fragments can be produced by enzymatic cleavage or by recombinant techniques. For example, papain or pepsin cleavage can generate Fab or F(ab')2 fragments, respectively. Other proteases with the requisite substrate specificity can also be used to generate Fab, F(ab')$_2$ or other antigen-binding fragments.

In embodiments, the antibody is a human or humanized α4β7 integrin antibody and the biologically functional fragment thereof is fragment of the human or humanized α4β7 integrin antibody. The process of humanizing antibodies is for administration to humans and is applied to monoclonal antibodies. Humanized antibodies are distinct from chimeric antibodies, since chimeric antibodies have a longer stretch of non-human protein. Methods for humanization of monoclonal antibodies are well-known and include the use of recombinant DNA to create constructs capable of expression in mammalian cell culture (Norderhaug et al., J. Immun. Methods, 204:77-87 (1997)). Other well-known methods include the use of a chimeric intermediate such as a mouse-human chimera, which is further humanized by selective alteration of the amino acids in the Fab portion of the molecule to retain the specificity for which the antibody is developed. Humanization can also be performed by inserting appropriate CDRs into encoding segments, responsible for the desired binding properties, into a human antibody scaffold using recombinant DNA methods (Reichmann et al., Nature, 332:323-327 (1998); Kashmiri et al, Methods 36:25-34 (2005); Hou et al., J. Biochem. 144:115-120 (2008)).

The humanized $α_4β_7$ integrin antibody can include an antigen binding region of nonhuman origin which binds α4β7 integrin and a constant region derived from a human constant region. The humanized α4β7 integrin antibody can also include a complementarity determining region of nonhuman origin which binds α4β7 integrin and a variable framework region of human origin, and optionally, a constant region of human origin. The humanized α4β7 integrin antibody can also include a heavy chain and a light chain, wherein the light chain includes a complementarity determining region derived from an antibody of nonhuman origin which binds α4β7 integrin and a framework region derived from a light chain of human origin, and the heavy chain includes a complementarity determining region derived from an antibody of nonhuman origin which binds 4β7 integrin and a framework region derived from a heavy chain of human origin.

In embodiments, the antigen binding region of the humanized antibody includes a CDR of nonhuman origin. The humanized antibody having binding specificity for α4β7 integrin includes at least one CDR of nonhuman origin. For example, CDRs can be derived from the light and heavy chain variable regions of immunoglobulins of nonhuman origin, such that a humanized immunoglobulin includes substantially heavy chain CDR1, CDR2 and/or CDR3, and/or light chain CDR1, CDR2 and/or CDR3, from one or more immunoglobulins of nonhuman origin, and the resulting humanized immunoglobulin has binding specificity for α4β7 integrin. In embodiments, all three CDRs of a selected chain are substantially the same as the corresponding chain of a donor, and/or all six CDRs of the light and heavy chains are substantially the same as the CDRs of the corresponding donor chains.

In embodiments, the portion of the humanized antibody which is of human origin (the human portion) can be derived from any suitable human immunoglobulin or immunoglobulin chain. For example, a human constant region or portion thereof, if present, can be derived from the κ or λ light chains, and or the γ (e.g., γI, γ2, γ3, γ4), μ, (e.g., I, α2), δ or ε heavy chains of human antibodies, including allelic variants. A particular constant region (e.g., IgGI), variant or portions thereof can be selected in order to tailor effector function. For example, a mutated constant region (variant) can be incorporated into a fusion protein to minimize binding to Fc receptors and/or ability to fix complement (see e.g., Winter et al, GB 2,209,757 B; Morrison et al, WO 89/07142; Morgan et al, WO 94/29351, Dec. 22, 1994).

The present disclosure describes methods of targeting the cofilin pathway using agents described herein to restore T cell motility, T cell tissue repopulation, and/or T cell migration and homing to lymphoid and non-lymphoid tissues. In embodiments, the T cell motility, T cell tissue repopulation, and/or T cell migration and homing to lymphoid and non-lymphoid tissues is necessary in response to an HIV infection.

The present disclosure also describes methods of targeting the cofilin pathway using agents described herein to promote CD4 T cell repopulation and/or to reverse hyperactivation of cofilin. In embodiments, the promotion of CD4 T cell repopulation and reversing hyperactivation of cofilin is necessary after an antiviral therapy.

The present disclosure describes targeting the cofilin pathway by administering or contacting cells with agents described herein that target the cofilin pathway and determining, measuring, and/or detecting T cell motility, T cell tissue repopulation, T cell migration and homing to lymphoid and non-lymphoid tissues, CD4 T cell repopulation, and/or cofilin deactivation (reversal of cofilin hyperactivation). Detecting cofilin deactivation includes detecting adequate cofilin phosphorylation and/or detecting adequate actin polymerization for inducing one or more T cell functions. Various in vitro cells have been used as models for in vivo HIV infected cells. Examples include HIV-infected CEM-SS cells, HIV-infected blood resting or activated CD4 T cells, HIV-infected A3R5 T cells, HIV-infected Jurkat T cells or HeLa JC53, and HIV-infected macrophages/microglia cells.

There are various known methods for determining, measuring, and/or detecting T cell motility, T cell tissue repopulation, T cell migration and homing to lymphoid and non-lymphoid tissues, CD4 T cell repopulation, and/or cofilin deactivation (reversal of cofilin hyperactivation). As an example, the in vitro chemotaxis assay can be used to determine T cell migration and T cell motility.

In embodiments, the cells used in the methods described herein are isolated from a biological sample of a subject infected with HIV. The biological sample can be body fluids. Examples of body fluids include blood, blood plasma, blood serum, vaginal secretion and discharge, cerebral spinal fluid, amniotic fluid, saliva, tear, sweat, and urine. The cells can be T cells, for example CD4 T cells, from a HIV-infected subject. When the cells are isolated from a biological sample, the targeting of the cofilin pathway is performed in an in vitro assay. In embodiments, the cells are in a subject, and the targeting of the cofilin pathway is by in vivo methods.

The present disclosure further describes methods of targeting the cofilin pathway to promote immune reconstitution and/or to promote immune control of viremia. The method includes administering an effective amount of an agent described herein to a subject in need thereof to promote immune reconstitution in the subject, and/or to promote immune control of viremia in the subject. Immune reconstitution and immune control of viremia refers to the restoration of T cell functions to achieve persistent control of HIV. Subjects characterized with immune reconstitution have a good CD4 T cell number after recovery, reduced chronic immune activation, and appear to be healthy. Subjects characterized with viremia control have no viral loads increase following the termination of antiretroviral therapy.

Furthermore, the present disclosure describes methods of treating AIDS or alleviating the symptoms caused by an HIV infection including administering an effective amount of an agent described herein to a subject in need thereof. In embodiments, the agent restores and/or promotes one or more of the following in the subject in need thereof: T cell motility, T cell tissue repopulation, T cell migration and homing to lymphoid and non-lymphoid tissues, CD4 T cell repopulation, cofilin deactivation (reversal of cofilin hyperactivation), immune reconstitution, and/or immune control of viremia. In embodiments, the agent is an integrin antibody, such as the α4β7 integrin antibody.

The present disclosure also describes methods of treating AIDS or alleviating the symptoms caused by an HIV infection by administering an agent described herein in combination with another therapy, for example, ART therapy. ART therapy involves taking a combination of antiretrovirals from at least two different drug classes every day. Antivirals are grouped into six different drug classes according to how they fight HIV. The six classes include non-nucleoside reverse transcriptase inhibitors (NNRTIs), nucleoside reverse transcriptase inhibitors (NRTIs), protease inhibitors (PIs), fusion inhibitors, CCR5 antagonists, and integrase inhibitors. Some anti-HIV medications are available in combination of two or more medications in one pill. Examples of antiretrovirals prescribed to subjects include Atripla (a combination of Sustiva (efavirenz or EFV; NRTI class), Emtriva (emtricitabine or FTC), and Viread (tenofovir or TDF)); Reyataz (atazanavir or ATV; PI class), Norvir (ritonavir or RTV; PI class), and Truvada ((a combination of Emtriva and Viread, both are from the NRTI class); Prezista (darunavir or DRV; PI class), Norvir, and Truvada; and Isentress (raltegravir or RAL; integrase inhibitor class) and Truvada.

The present disclosure describes compositions and pharmaceutical compositions including the agent that targets the cofilin pathway for administering to cells and subjects. The compositions or pharmaceutical compositions described herein include the agent and a carrier or a pharmaceutically acceptable carrier, respectively.

The pharmaceutical compositions described herein include a therapeutically effective amount of the therapeutic agent and a pharmaceutically acceptable carrier. The pharmaceutical compositions are formulated to be suitable for the route of administration to a subject. The therapeutic agent, such as an agent that targets the cofilin pathway, for example, the α4β7 integrin antibody or fragment thereof, can be formulated as various dosage forms to contain a therapeutically effective amount for administration. The pharmaceutical composition including the therapeutic agent described herein can be administered in combination with ART.

The dosage of the agents to be administered to a subject will vary with the precise stage of the AIDS being treated and the recipient of the treatment. The scaling of dosages for human administration can be performed according to art-accepted practices by a physician depending on various factors. In embodiments, the administration of an amount of agent, such as an antibody or a fragment thereof, in a particular dose as well as the interval between doses can depend on the characteristics of the individual, such as general health, age, sex, body weight and tolerance to drugs as well as the type and severity of AIDS, The human or humanized antibody or fragment thereof can be administered to a subject alone or in conjunction with another agent. In embodiments, a human or humanized antibody or fragment of the α4β7 integrin antibody for the treatment of AIDS can be administered alone or before, along with, or subsequent to administration of the medication(s) used in the ART.

In embodiments, about 0.1 mg to about 500 mg of the antibody per kg body weight is administered during a period of about 1-3 months. The interval between any two doses can independently vary from a few minutes to about 30 days or more. When a fragment of a human or humanized antibody is to be administered, the amount which is administered during the period of about one month can be adjusted in accordance with the size of the fragment.

The amount of human or humanized antibody or fragments thereof to be administered in each dose can be an amount which is effective to produce a desired pharmacokinetic or pharmacodynamic effect. A variety of pharmacokinetic and pharmacodynamic parameters of human and/or humanized antibodies or fragments thereof can be measured using suitable methods. For instance, pharmacodynamic parameters of antibodies and fragments thereof, such as antigen saturation, antibody-induced inhibition of expression of antigen, can be measured using a suitable immunoassay. For example, the α4β7 signal (i.e., binding of labeled antibody to α4β7) following administration of the antibody can be measured by flow cytometry to determine targeting of the cofilin pathway. Other methods include detecting and/or measuring the effects on T cell chemotaxis, and the effects on cofilin phosphorylation using Western blots.

The present disclosure also describes methods of screening drugs that target the cofilin pathway. The methods include contacting a candidate drug with a sample of HIV infected T cells and detecting regulation of the cofilin pathway by the candidate drug. Detecting regulation of the cofilin pathway includes detecting the candidate drug enhancing or reducing cofilin phosphorylation and/or enhancing actin polymerization or actin depolymerization. Detecting regulation of the cofilin pathway also includes detecting enhancement or restoration of T cell motility, T cell tissue repopulation, T cell migration and homing to lymphoid and non-lymphoid tissues, CD4 T cell repopulation, and/or cofilin deactivation (reversal of cofilin hyperactivation). As an example, detecting T cell motility and T cell migration can be performed using the in vitro trans-well migration assay. Detecting regulation of the cofilin pathway by the candidate drug can be compared to a control, such as by α4β7 integrin antibody, a known agent that targets the cofilin pathway.

The drug screening methods disclosed herein can also be performed in a competition assay using a known agent that targets the cofilin pathway, such as the α4β7 integrin antibody, and the candidate drug to determine how the candidate drug competes with the α4β7 integrin antibody for targeting the cofilin pathway.

Methods disclosed herein include treating subjects such as mammals. Examples of mammals include human, chimpanzes, monkeys, dogs, cats, mice, rats, and transgenic species thereof. Subjects in need of a treatment (in need thereof) are subjects infected with HIV. The terms "patient," "subject,"

and "individual," and the like are used interchangeably herein, and refer to any mammal, amenable to the methods described herein. In embodiments, the patient, subject, or individual is a human.

The term "bind," "binds," or "interacts with" refers to a molecule recognizing and adhering to a particular second molecule in a sample or organism but does not substantially recognize or adhere to other structurally unrelated molecules in the sample. The term "specifically binds," as used herein with respect to an antibody, refers to an antibody which recognizes a specific antigen, but does not substantially recognize or bind other molecules in a sample.

The term "carrier" refers to a diluent, adjuvant (e.g., Freund's adjuvant (complete and incomplete)), excipient, or vehicle with which the therapeutic is administered. Pharmaceutical carriers can be sterile liquids, such as water and oils, including those of petroleum, animal, vegetable or synthetic origin, such as peanut oil, soybean oil, mineral oil, sesame oil and the like. Water is usually used as the carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. For the use of further excipients, please also see "Handbook of Pharmaceutical Excipients", fifth edition, R. C. Rowe, P. J. Seskey and S. C. Owen, Pharmaceutical Press, London, Chicago. The composition, if desired, can also contain minor amounts of wetting or emulsifying agents, or pH buffering agents. These compositions can take the form of solutions, suspensions, emulsion, tablets, pills, capsules, powders, sustained-release formulations and the like. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in "Remington's Pharmaceutical Sciences" by E. W. Martin. Such compositions will contain a therapeutically effective amount of the agent, preferably in purified form, together with a suitable amount of carrier so as to provide the form for proper administration to the patient. The formulation should suit the mode of administration.

The pharmaceutical composition described herein can be formulated into various dosage forms including solid dosage forms for oral administration such as capsules, tablets, pills, powders and granules, liquid dosage forms for oral administration such as pharmaceutically acceptable emulsions, microemulsions, solutions, suspensions, syrups and elixirs, injectable preparations, for example, sterile injectable aqueous or oleaginous suspensions, compositions for rectal or vaginal administration, preferably suppositories.

Pharmaceutical compositions may be administered in a manner appropriate treatment of AIDS or alleviation of symptoms of AIDS. The quantity and frequency of administration will be determined by such factors as the condition of the subject, and the type and severity of the AIDS, although appropriate dosages may be determined by clinical trials.

The administration of the pharmaceutical compositions described herein may be carried out in any convenient manner, including by aerosol inhalation, injection, ingestion, transfusion, implantation or transplantation. The pharmaceutical compositions described herein may be administered to a patient subcutaneously, intradermally, intratumorally, intranodally, intramedullary, intramuscularly, by intravenous (i. v.) injection, or intraperitoneally.

The term "therapeutically effective amount" refers to the amount of an agent that will elicit the biological or medical response of cells, tissue, system, or subject that is being sought by the researcher, veterinarian, medical doctor or another clinician. The term "therapeutically effective amount" includes that amount of a compound that, when administered, is sufficient to alleviate to some extent, one or more of the signs or symptoms of AIDS. The therapeutically effective amount will vary depending on the agent, the severity and stage of AIDS, and the age, weight, etc., of the subject to be treated.

Ranges: throughout this disclosure, various aspects of the disclosure can be presented in a range format. It should be understood that the description in range format is merely for convenience and brevity and should not be construed as an inflexible limitation on the scope of the disclosure. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

Ranges described throughout the application include the specified range, the sub-ranges within the specified range, the individual numbers within the range, and the endpoints of the range. For example, description of a range such as from one or more up to 173 includes subranges such as from one or more to 100 or more, from 10 or more to 20 or more, from one or more to five or more, as well as individual numbers within that range, for example, 1, 2, 3, 4, 5, 10, 20, 100, and 173.

By "statistically significant," it is meant that the result was unlikely to have occurred by chance. Statistical significance can be determined by any method known in the art. Commonly used measures of significance include the p-value, which is the frequency or probability with which the observed event would occur if the null hypothesis were true. If the obtained p-value is smaller than the significance level, then the null hypothesis is rejected. In simple cases, the significance level is defined at a p-value of 0.05 or less. A "decreased" or "reduced" or "lesser" amount is typically a "statistically significant" or a physiologically significant amount, and may include a decrease that is about 1.1, 1.2, 1.3, 1.4, 1.5, 1.6, 1.7, 1.8, 1.9, 2, 2.5, 3, 3.5, 4, 4.5, 5, 6, 7, 8, 9, 10, 15, 20, 30, 40, or 50 or more times (e.g., 100, 500, 1000 times) (including all integers and decimal points in between and above 1, e.g., 1.5, 1.6, 1.7, 1.8, etc.) an amount or level described herein.

Each embodiment disclosed herein can comprise, consist essentially of or consist of its particular stated element, step, ingredient or component. Thus, the terms "include" or "including" should be interpreted to recite: "comprise, consist of, or consist essentially of." The transition term "comprise" or "comprises" means includes, but is not limited to, and allows for the inclusion of unspecified elements, steps, ingredients, or components, even in major amounts. The transitional phrase "consisting of" excludes any element, step, ingredient or component not specified. The transition phrase "consisting essentially of" limits the scope of the embodiment to the specified elements, steps, ingredients or components and to those that do not materially affect the embodiment.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present disclosure At the very least, and not as an attempt to limit the application of the doctrine of equivalents to the scope of the claims, each numerical parameter should at least be construed in light of the number of reported significant digits and by applying ordinary rounding techniques. When further clarity is required, the term "about" has the meaning reasonably ascribed to it by a person skilled in the art when used in conjunction with a stated numerical value or range, i.e. denoting somewhat more or somewhat less than the stated value or range, to within a range of ±20% of the stated value; ±19% of the stated value; ±18% of the stated value; ±17% of the stated value; ±16% of the stated value; ±15% of the stated value; ±14% of the stated value; ±13% of the stated value; ±12% of the stated value; ±11% of the stated value; ±10% of the stated value; ±9% of the stated value; ±8% of the stated value; ±7% of the stated value; ±6% of the stated value; ±5% of the stated value; ±4% of the stated value; ±3% of the stated value; ±2% of the stated value; or ±1% of the stated value.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

The present disclosure is further described by reference to the following exemplary embodiments and examples. These exemplary embodiments and examples are provided for purposes of illustration only and are not intended to be limiting unless otherwise specified. Thus, the present disclosure should in no way be construed as being limited to the following exemplary embodiments and examples, but rather, should be construed to encompass any and all variations which become evident as a result of the teaching provided herein.

Exemplary Embodiments

The following are exemplary embodiments:
1. A method of restoring T cell motility, wherein the method includes targeting cofilin pathway.
2. A method of restoring T cell migration and homing to lymphoid and non-lymphoid tissues, wherein the method comprises targeting cofilin pathway.
3. A method of restoring T cell tissue repopulation, wherein the method comprises targeting cofilin pathway.
4. A method of promoting CD4 T cell repopulation, wherein the method comprises targeting cofilin pathway.
5. A method of reversing hyperactivation of cofilin, wherein the method comprises targeting cofilin pathway.
6. The method of any one embodiments 1-5, wherein targeting the cofilin pathway includes administering to cells infected with HIV with an agent that targets the cofilin pathway.
7. The method of embodiment 6, wherein the agent is a protein.
8. The method of embodiment 7, wherein the protein is an antibody or a fragment thereof.
9. The method of embodiment 8, wherein the antibody is α4β7 integrin antibody.
10. The method of embodiment 9, wherein the antibody is a human α4β7 integrin antibody or a humanized α4β7 integrin antibody.
11. The method of any one of embodiments 6-10, wherein the cells are obtained from a biological sample of a subject infected with HIV.
12. The method of any one of embodiments 6-10, wherein the cells are in a subject infected with HIV.
13. The method of any one of embodiments 1-12, wherein the method is performed after treating the subject with ART.
14. The method of any one of embodiments 1-13, wherein the method includes detecting, or measuring T cell motility, T cell migration and homing to lymphoid and non-lymphoid tissues, T cell tissue repopulation, CD4 T cell repopulation, and/or the method includes detecting or measuring reversal of cofilin hyperactivation.
15. The method of any one of embodiments 1-14, wherein the method further includes comparing with a control to show T cell motility, T cell migration and homing to lymphoid and non-lymphoid tissues, T cell tissue repopulation, CD4 T cell repopulation, and/or reversal of cofilin hyperactivation.
16. The method of embodiment 15, wherein the control includes cells from the same subject but untreated with the agent or from a healthy subject untreated with the agent.
17. A method of treating a subject infected with HIV, wherein the method provides immune reconstitution.
18. A method of treating a subject infected with HIV, wherein the method provides immune control of viremia.
19. A method of treating a subject infected with HIV, wherein the method restores one or more T cell functions.

20. The method of any one of embodiments 17-19, wherein the method includes administering to the subject an agent that targets cofilin pathway.
21. The method of embodiment 20, wherein the agent is a protein.
22. The method of embodiment 21, wherein the protein is an antibody or a fragment thereof.
23. The method of embodiment 22, wherein the antibody is α4β7 integrin antibody.
24. The method of embodiment 23, wherein the antibody is a human α4β7 integrin antibody or a humanized α4β7 integrin antibody.
25. The method of any one of embodiments 17-24, wherein the method restores or promotes T cell motility, T cell migration and homing to lymphoid and non-lymphoid tissues, T cell tissue repopulation, and/or CD4 T cell repopulation, and/or cofilin deactivation in the subject.
26. The method of any one of embodiments 17-25, wherein the method further includes treating the subject prior to, subsequent to, or at the same time with antiretroviral therapy (ART).
27. A method of screening for drugs that target cofilin pathway, wherein the method comprises contacting a candidate drug with HIV infected T cells and detecting regulation of cofilin pathway by the candidate drug.
28. The method of embodiment 27, wherein detecting regulation of the cofilin pathway comprises detecting the candidate drug enhances or reduces cofilin phosphorylation and/or enhances actin polymerization or actin depolymerization.
29. The method of embodiment 27 or 28, wherein detecting regulation of the cofilin pathway comprises detecting the candidate drug promotes or restores one or more T cell functions.
30. The method of any one of embodiments 27-29, wherein the one or more T cell functions are T cell motility, T cell migration and homing to lymphoid and non-lymphoid tissues, T cell tissue repopulation, and/or CD4 T cell repopulation, and/or cofilin deactivation in the subject.
31. The method of any one of embodiments 27-30, wherein the method further includes comparing the regulation of the cofilin pathway with a known agent that targets the colfilin pathway.
31. The method of embodiment 30, wherein the agent is a human α4β7 integrin antibody or a humanized α4β7 integrin antibody.

EXAMPLES

Example 1

In the human immune system, T cell activity is mainly regulated by receptor signaling. Persistent signaling through cytokine or chemokine receptors frequently leads to T cell commitment into distinct lineages such as Th1, Th2, or Th17. In HIV infection, the virus infects T cells through gp120 binding to CD4 and the chemokine co-receptor CXCR4 or CCR5 (15). Such binding also initiates signaling and may have pathogenic consequences (14). In particular, HIV signaling through CXCR4 has been shown to activate an actin depolymerizing factor, cofilin, to promote actin dynamics for viral nuclear entry (13, 16). Cofilin is an actin-binding protein that binds and depolymerizes filamentous actin (F-actin) to regulate actin treadmilling (16, 17), a process in which monomeric actin (G-actin) is incorporated in F-actin at the (+) end, and then dissociated from the (−) end. In T cells, cofilin regulates the actin dynamics required for T cell motility and T cell migration and homing to lymphoid tissues (18). The migratory defects seen in the CD4 T cells of HIV infected patients may be associated with cofilin dysregulation resulting from persistent CXCR4 signaling by HIV (19).

In addition to CXCR4, CCR5 is used by R5-tropic viruses that predominate early in the infection; R5 HIV infects and depletes gut memory CD4 T cells, leading to chronic immune activation (20, 21). Whether HIV-mediated CCR5 signaling can also lead to cofilin activation in memory T cells was investigated. In contrast to X4 viruses, which infect both memory and naïve CD4 T cells, R5 viruses infect a subpopulation of memory CD4 T cells (FIG. 1A). CCR5 is present on only around 30% of resting memory CD4 T cells (FIG. 1B). Given this low percentage, a flow cytometry-based intracellular phospho-cofilin staining method was used to quantify cofilin in individual cells. Blood resting memory CD4 T cells were purified and stimulated with an R5 virus, HIV(AD8) (FIG. 1C), or an R5 HIV envelope protein, gp120(BAL) (FIG. 1D). Dephosphorylation of cofilin following exposure of memory T cells to the R5-HIV was observed; this cofilin activation is mediated through Gαi, as pertussis toxin largely abrogated late cofilin activation (FIG. 1C). In addition, when resting CD4 T cells were similarly stimulated with an R5 gp120, gp120(BAL), similar cofilin activation was observed, demonstrating that gp120 itself is sufficient to trigger cofilin activation (FIG. 1D). Furthermore, when cells were pretreated with the CCR5 blocker, maravoric, cofilin activation was also largely abrogated (FIG. 1D). In conclusion, R5 gp120 binding to CCR5 also triggers Gαi signaling that leads to the activation of cofilin. Thus, both X4 and R5 viruses activate cofilin by signaling through their respective chemokine coreceptors.

Example 2

It has been demonstrated that one or two virion particles are sufficient to trigger chemotactic signaling (22). Given that patients' CD4 T cells are chronically exposed to gp120 (23-25), particularly during the acute phase, we investigated whether persistent signaling may alter the cofilin pathway (13, 26). A large blinded clinical trial was conducted to examine cofilin phosphorylation in blood resting CD4 T cells (FIG. 2A). For this purpose, a reverse phase phospho-cofilin micro-array was developed that can quantify cofilin phosphorylation in a large number of clinical samples simultaneously (27) (FIG. 2B). Blood resting CD4 T cells from HIV patients (Table S1), with ART (HIV+ART, n=95) or without ART (HIV, n=98), or from healthy controls (HC, n=100) were purified by negative depletion, unstimulated, and then lysed. Blindly coded cell lysates were then profiled with the phospho-cofilin micro-array (FIG. 2C). A highly significant reduction in cofilin phosphorylation in HIV patients (HIV=0.968; HIV+ART=1.139; healthy control=2.254; p<0.001) was observed. Surprisingly, ART does not significantly restore cofilin phosphorylation (HIV=0.968; HIV+ART=1.139; p=0.981). These results suggest that HIV infection leads to cofilin dephosphorylation in blood CD4 T cells that polarizes the cells towards an ART-irreversible pathogenic phenotype. In untreated patients, there is only a weak correlation between cofilin phosphorylation and viral load (p=0.043, r=−0.205) (FIG. 2D), and there is no correlation between cofilin phosphorylation and CD4 T cell counts (p=0.057, r=0.193) (FIG. 2E).

TABLE S1

Characteristics of clinical study participants.

| | HIV | HIV + ART | HC | P Value |
|---|---|---|---|---|
| No. of participants | 98 | 95 | 100 | — |
| Han ethnicity, no. (%) | 98 (100) | 95 (100) | 100 (100) | — |
| Male sex, no. (%) | 98 (100) | 95 (100) | 100 (100) | — |
| Age, mean (SD), years | 36 (10) | 37 (11) | 34 (11) | 0.167 |
| CD4 counts, mean (SD), cells/µl | 361 (196) | 378 (141) | — | 0.476 |
| Viral load, mean (SD), log copies/ml | 4.49 (0.71) | 0.90 (0.87) | — | <0.001 |

Example 3

Figure 3:
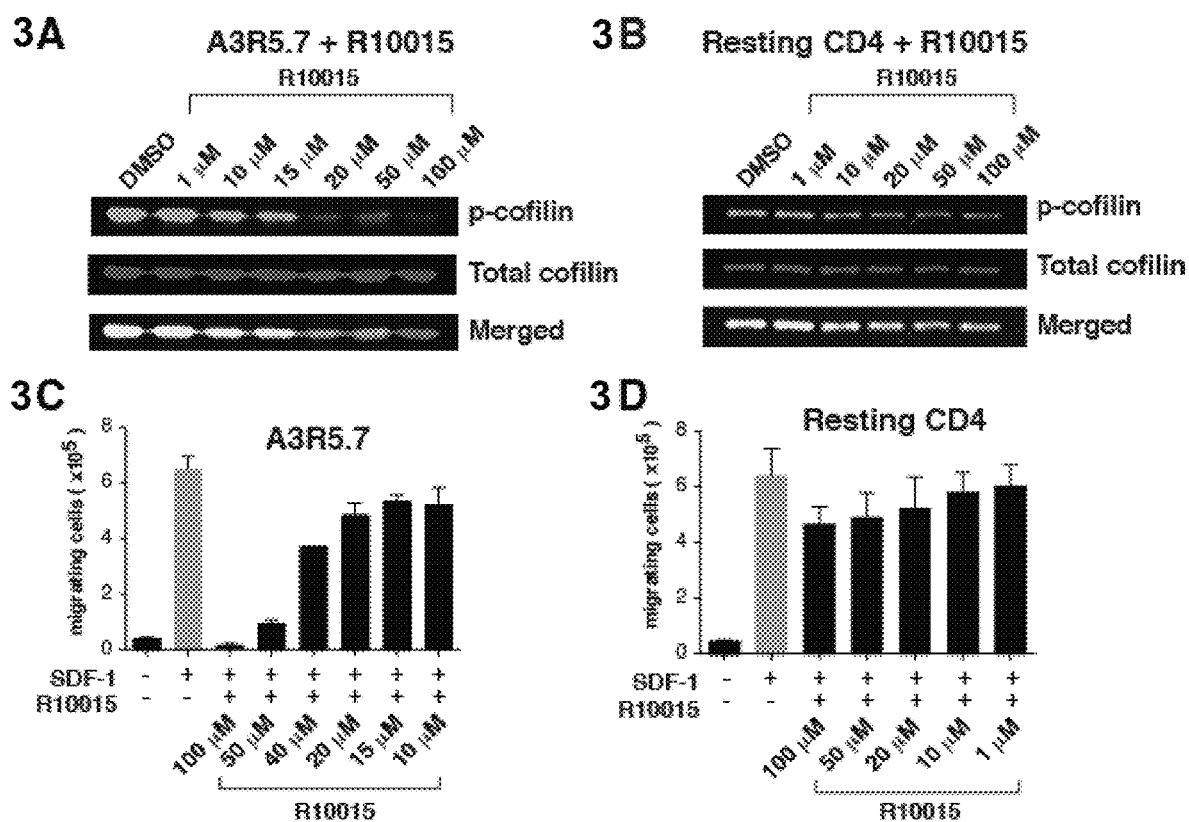
FIGS. 3A-3D show quantification of the effects of cofilin on T cell chemotaxis. (A) A3R5.7 T cells or (B) blood resting CD4 T cells were treated with different dosages of R10015 for one hour. Phospho-cofilin and total cofilin were quantified by Western blot. (C and D) R10015 inhibits cofilin phosphorylation and T cell chemotaxis in response to SDF-1. A3R5.7 (C) or blood resting CD4 T cells (D) were treated with different dosages of R10015 for one hour, and then added to the upper chamber of a 24-well trans-well plate. The lower chamber was filled with SDF-1 (40 ng/ml), and cell migration to the lower chamber was quantified.

Cofilin hyperactivation may be associated with a migratory impairment of CCR6+ and CXCR3+ helper T cells (Th), which are prevented from trafficking from the blood stream to peripheral organs even in aviremic HIV patients on long-term ART (5). T cell migration and homing is controlled by chemotactic signaling which activates cycles of cofilin phosphorylation and dephosphorylation to drive actin dynamics for cell motility. Phosphorylation of cofilin is regulated by LIM-domain kinase (LIMK), which inactivates cofilin through serine 3 phosphorylation (28). To quantify the effect of cofilin hyperactivation on T cell migration, a recently discovered LIMK inhibitor, R10015 (29) was used, to mimic cofilin activation in HIV infection. A human CD4 T cell line, A3R5.7, or blood resting CD4 T cells were treated with different dosages of R10015 during chemotaxis (FIG. 3). A R10015 dosage-dependent dephosphorylation of cofilin was observed (FIGS. 3A and 3B), and this dephosphorylation correlates with the R10015 dosage-dependent impairment of T cell chemotaxis (FIGS. 3C and 3D). At around 15 to 20 µM of R10015, cofilin phosphorylation was reduced to around 50%, approximately the level seen in HIV patients (FIGS. 3A and 3B). A 50% reduction in cofilin phosphorylation resulted in a 20-40% decrease in migrating T cells for A3R5.7 and blood T cells (FIGS. 3C and 3D). These results suggest that the reduction in cofilin phosphorylation can cause a partial impairment of T cell motility that may affect T cell trafficking to lymphoid and non-lymphoid tissues, as seen in HIV patients (5, 6).

Example 4

To target the cofilin pathway, a marine toxin, okadaic acid (OA), that can activate LIMK and enhance cofilin phosphorylation and actin polymerization was previously identified (30). In a proof-of-concept study, OA was used to target the cofilin pathway to restore T cell migration, both in vitro and in vivo in a murine model (5). The high toxicity of OA prevents its therapeutic use to restore T cell motility. However, in a recent SIV/macaque study, the use of an anti-α4β7 integrin antibody surprisingly promoted effective repopulation of CD4 T cells in a wide variety of immune tissues including gastro-intestinal tissues (GITs) (31). Integrins are cell surface adhesion molecules that mediate the cell-extracellular matrix and cell-cell interactions that facilitate T cell trafficking and homing to tissues (32). This process involves synergistic, bi-directional signaling with chemokine receptors (inside-out and outside-in signaling) (33, 34). Stimulation of chemokine receptors triggers chemotactic signaling that leads to the assembly of an intracellular complex connecting integrins to the actin cytoskeletons for integrin activation (inside-out signaling). Binding of active integrins to ligands triggers further signals that lead to actin cytoskeletal rearrangement for cell spreading, retraction, and migration (outside-in signaling) (35). Given that the anti-α4β7 integrin antibody promoted T cell trafficking and homing to lymphoid tissues in SIV infection (31), whether stimulation of T cells with an anti-α4β7 antibody may trigger a similar outside-in signaling to modulate the cofilin pathway and promote T cell motility was investigated.

Figure 4:
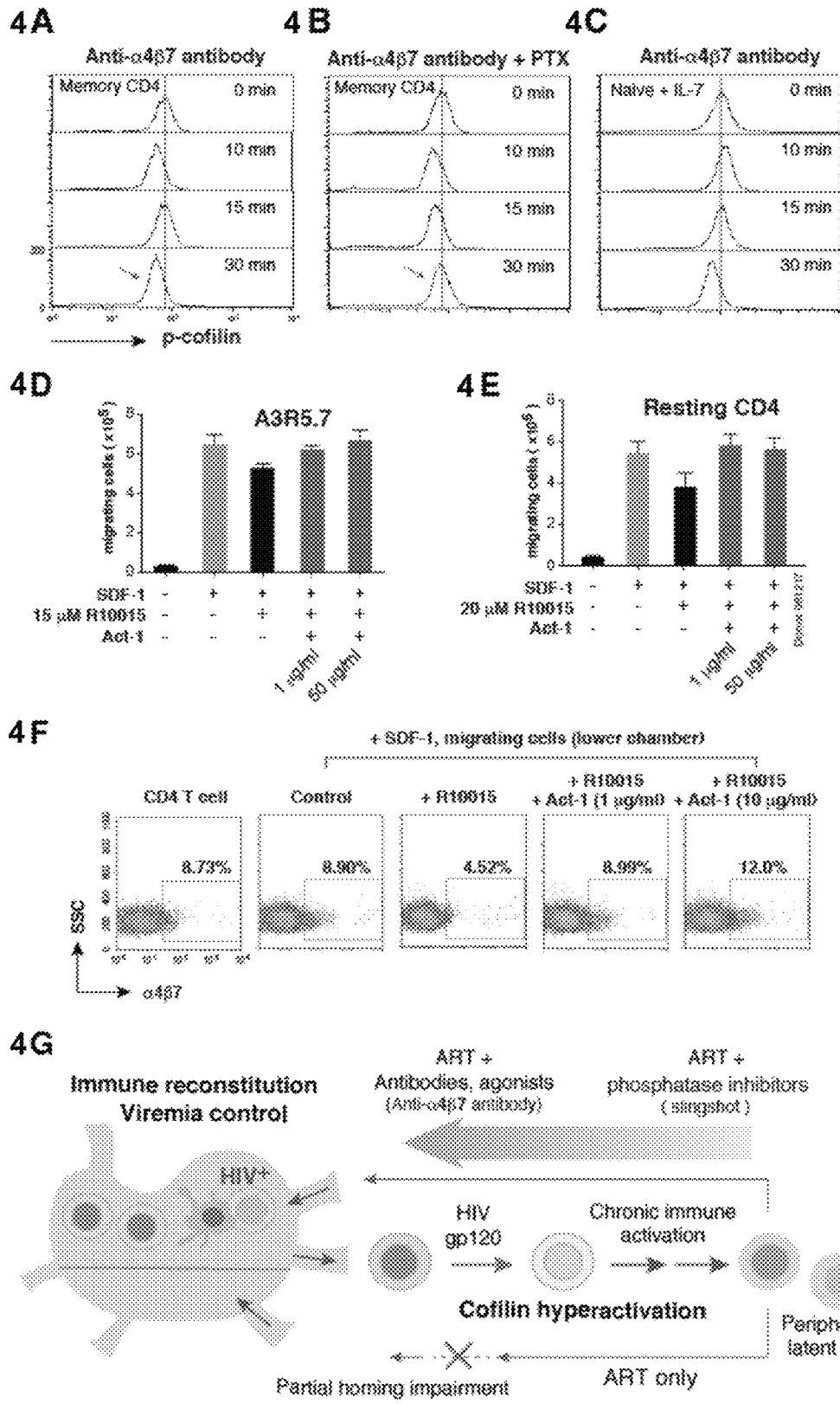
FIGS. 4A-4G show Targeting the cofilin pathway using an anti-human α4β7 antibody. (A to C) The anti-human α4β7 antibody, Act-1, modulates the cofilin pathway through pertussis toxin (PTX)-sensitive Gαi signaling. Resting memory CD4 T cells (A and B) were not treated (A) or treated with PTX (B) for 2 hours, and then stimulated with Act-1 (1 μg/ml) for various times. (C) Naïve CD4 T cells (cultured in IL-7) were also similarly stimulated with Act-1. Cofilin phosphorylation was quantified by intracellular staining and flow cytometry. (D and E) Act-1 promotes T cell chemotaxis. A3R5.7 T cells (D) or human blood resting CD4 T cells (E) were pre-treated with R10015 or DMSO for 1 hour, and then stimulated with Act-1 or a control mouse IgG for an additional 15 minutes. Cells were then added to the upper chamber of a 24-well trans-well plate. The lower chamber was filled with SDF-1 (40 ng/ml). Cell migration to the lower chamber was quantified. (F) Act-1 selectively promotes the migration of the α4β7+ CD4 T cells. Migrating T cells in the lower chamber were stained with an anti-α4β7 antibody, followed by staining with Alexa Fluor 647-conjugated goat anti-mouse secondary antibodies. (G) Model of cofilin hyperactivation in HIV infection and therapeutic targeting of the cofilin pathway. Early HIV signaling through chemokine coreceptors (CCR5 and CXCR4) and late chronic immune activation may trigger cofilin hyperactivation, impairing CD4 T cell homing to lymphoid tissues such as GALT. ART alone is not sufficient to restore T cell homing. Targeting the cofilin pathway through antibodies (stimulating chemotactic receptors such as the α4β7 integrin), receptor agonists, the LIMK kinase activators (such as okadaic acid), or the cofilin phosphatase (slingshot) inhibitors may restore T cell homing, leading to immune reconstitution and immune control of viremia.
Figure 5:
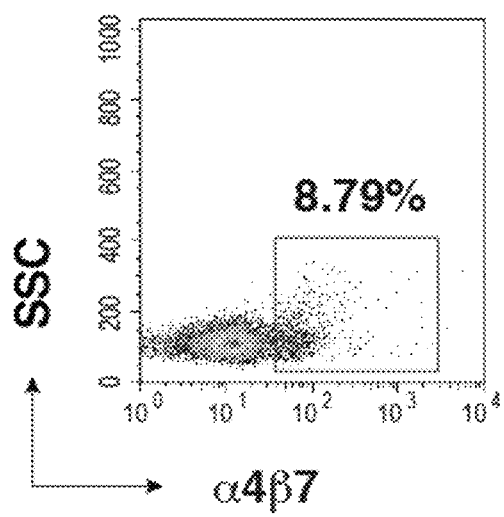
FIGS. 5A and 5B show surface expression of α4β7 on different subsets of human blood resting CD4 T cells, as measured by surface staining and flow cytometry. (A) Purified memory CD4 T cells were stained with an anti-α4β7 antibody (Act-1), following by staining with Alexa Fluor 647-conjugated goat anti-mouse secondary antibodies. (B) Purified naïve CD4 T cells were similar stained with the anti-α4β7 antibody. For comparison, resting naïve T cells were also cultured in IL-7 for 3 days, and stained with the anti-α4β7 antibody.
Figure 5:
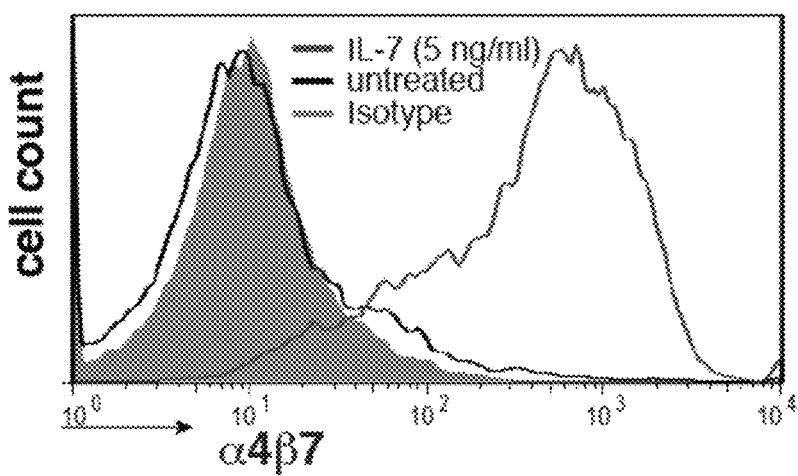

In the human peripheral blood, high levels of α4β7 were detected on a subpopulation of resting memory CD4 T cells (36). In addition, culturing naïve T cells in IL-7 can greatly upregulate α4β7 on the cell surface (36) (FIG. 5). Resting memory and IL-7-cultured naïve T cells were stimulated with an anti-human α4β7 antibody (Act-1), and it was observed that this low dosage of Act-1 (1 µg/ml) can directly trigger cofilin phosphorylation and dephosphorylation in a time course (FIG. 4A to 4C), demonstrating that the α4β7 antibody is capable of modulating the cofilin pathway. Chemokine and integrin-mediated T cell rolling and migration have been shown to be dependent on G protein signaling, particularly Gαi, which can be inhibited by pertussis toxin (PTX) (37). Memory T cells were treated with PTX and observed late inhibition of cofilin activation by PTX (30 min in FIG. 4B), demonstrating that the α4β7 antibody-mediated transient cofilin activity is partially dependent on Gαi signaling.

Figure 6:
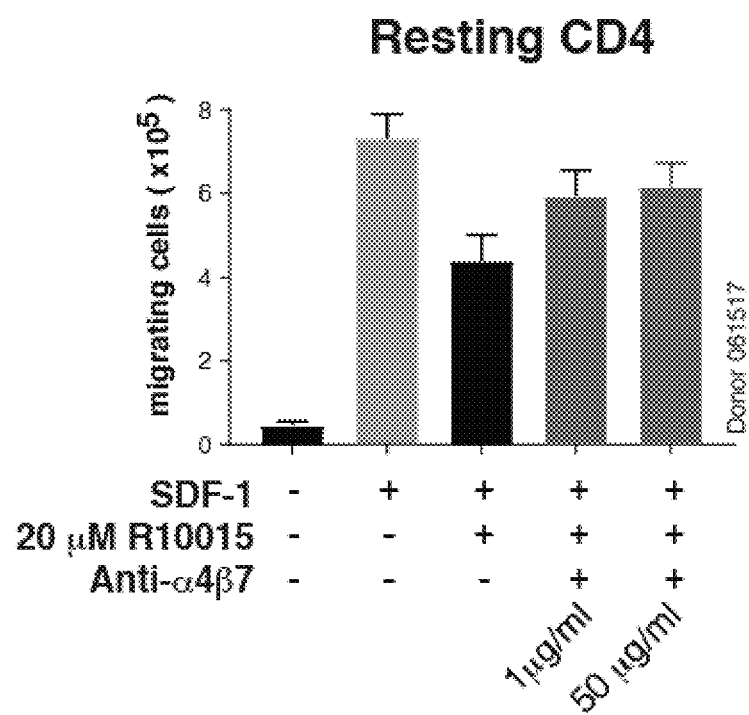
FIG. 6 shows anti-human α4β7 antibody Act-1 promotes T cell chemotaxis. Human blood resting CD4 T cells were pre-treated with R10015 or DMSO for 1 hour, and then stimulated with Act-1 or a control mouse IgG for an additional 15 minutes. Cells were added to the upper chamber of a 24-well trans-well plate. The lower chamber was filled with SDF-1 (40 ng/ml). Cell migration to the lower chamber was quantified.
Figure 7:
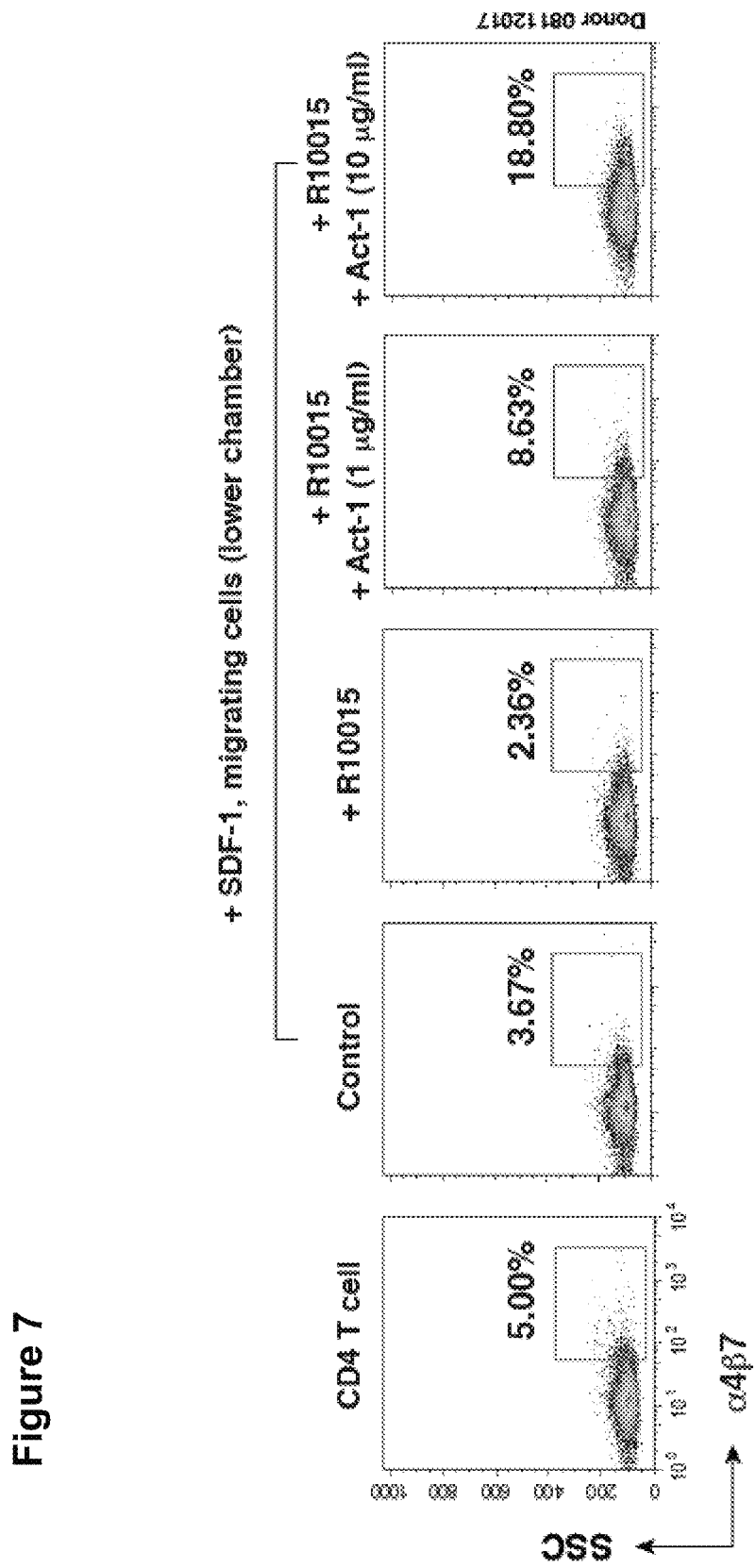
FIG. 7 shows Act-1 selectively promotes the migration of the α4β7+ CD4 T cells. Human blood resting CD4 T cells were pre-treated with R10015 or DMSO (control) for 1 hour, and then stimulated with Act-1 or a control mouse IgG for an additional 15 minutes. Cells were then added to the upper chamber of a 24-well trans-well plate. The lower chamber was filled with SDF-1 (40 ng/ml). Cell migration to the lower chamber was analyzed by staining with an anti-α4β7 antibody, Act-1, following by staining with Alexa Fluor 647-conjugated goat anti-mouse secondary antibodies.
Figure 8:
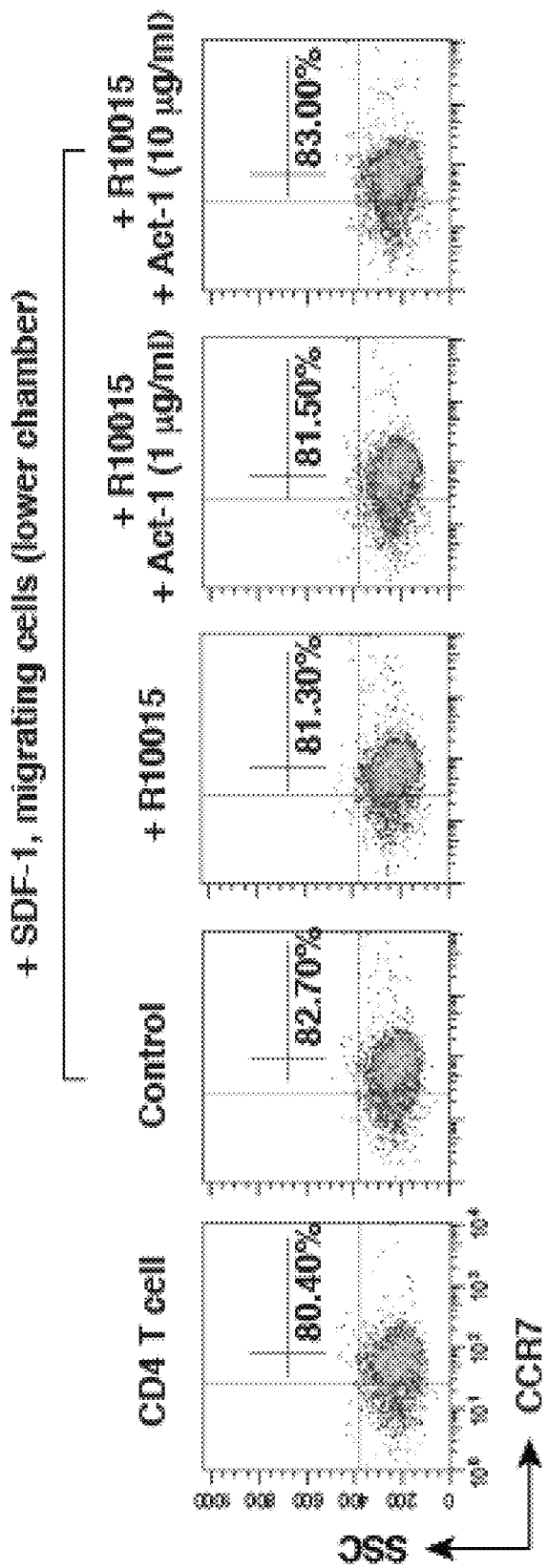
FIG. 8 shows Act-1 does not selectively promote the migration of CCR7+ CD4 T cells. Human blood resting CD4 T cells were pre-treated with R10015 or DMSO (control) for 1 hour, and then stimulated with Act-1 or a control mouse IgG for an additional 15 minutes. Cells were then added to the upper chamber of a 24-well trans-well plate. The lower chamber was filled with SDF-1 (40 ng/ml). Cell migration to the lower chamber was analyzed by staining with a PerCP-labeled anti-CCR7 antibody.

Next, whether the α4β7 antibody is capable of restoring the T cell migratory defects resulting from cofilin hyperactivation was investigated. First, to mimic cofilin dephosphorylation in HIV infection, 15 µM or 20 µM R10015 was used to reduce cofilin phosphorylation to around 50% in A3R5.7 or blood resting CD4 T cells (FIG. 3). With these R10015 dosages, there is a 20 to 40% reduction in cell migration (FIGS. 4D and 4E, FIG. 6). The use of low dosages (1-50 µg/ml) of Act-1 promoted T cell migration (FIGS. 4D and 4E, FIG. 6), demonstrating the capacity of the anti-α4β7 antibody to promote T cell motility and compensate the migratory defects resulting from cofilin hyperactivation. In the SIV/macaque model, the use of the anti-α4β7 antibody (50 mg/kg) led to an approximately 0.5- to 1.5-fold increase in the maximal regional signal representing CD4 T cell repopulation (31). In the chemotaxis trans-well assay, Act-1 stimulated a maximal 0.6-fold increase in total CD4 T cell migration, an increase that is within the enhancement range seen in the in vivo study (31). Whether Act-1 specifically promoted the migration of the α4β7+ CD4 T cells was further investigated by examining the cell subpopulation migrated to the lower chamber of the trans-well plate (FIG. 4F and FIG. 7). While R10015 inhibited the migration of all T cell subtypes, surprisingly, it had a greater inhibition of the α4β7$^{high}$ CD4 T cells, selectively diminishing the migration of the α4β7$^{high}$ T cells (from 8.90% to 4.52%) (FIG. 4F). Act-1 effectively restored T cell migration and increased the percentage of migrating α4β7$^{high}$ T cells from 4.52% to 12.0% (FIG. 4F). For comparison, the percentage of the CCR7+ T cell subpopulation was not altered by R10015 and Act-1 (FIG. 8). These results demonstrated that the motility of α4β7+ CD4 T cells is prone to inhibition through persistent blocking of cofilin phosphorylation; the α4β7+ CD4 T cells likely have a higher sensitivity to R10015- or HIV-mediated cofilin hyperactivation. This cofilin-mediated migratory impairment can be rescued by the anti-α4β7 antibody that may act through synergistic signaling with chemokines to modulate the cofilin pathway.

Example 5

It has long been speculated that HIV binding to the chemokine coreceptors may trigger aberrant G protein signaling and lead to CD4 T cell pathogenesis (15). Nevertheless, this speculation has not been solidified by experimental or clinical data. In this large clinical trial, we have demonstrated a high level of cofilin dephosphorylation in the blood CD4 T cells of HIV-infected patients. Cofilin has been identified as a direct downstream target of HIV-mediated G protein signaling through the chemokine coreceptors (13). Cofilin hyperactivation can directly affect two fundamental biological processes of T cells, T cell migration and activation (18, 38, 39). In HIV infection, selective impairment of CD4 but not CD8 T cell homing to lymphoid tissues (5, 7) is a hallmark of HIV-mediated CD4 T cell dysfunctions (6, 40), and this implies a direct role of cofilin dysregulation in HIV-mediated CD4 T cell pathogenesis. The molecular cue for cofilin hyperactivation likely results from early viral signaling from HIV gp120 (13) and chronic immune activation later in the disease course (5) that may exacerbate and polarize CD4 T cells towards ART-irreversible pathogenic lineages.

It was further demonstrated that the anti-human $\alpha 4\beta 7$ integrin antibody Act-1 can modulate the cofilin pathway, thereby promoting T cell motility. Although high dosages of anti-integrin antibodies can block integrin-ligand interaction and inhibit cell migration, these antibodies may also initiate an "outside-in" signal, as demonstrated above (FIG. 4A to 4C). In particular, if integrins are not completely sealed by antibodies at a saturating dosage, such antibody-induced signaling may synergize with chemokine signaling to promote cell motility. Antibody-induced signaling has been shown to enhance HIV latent infection of T cells; while high dosages of an anti-CXCR4 antibody block HIV binding and entry, at low dosages, the same antibody triggers CXCR4 signaling and enhances HIV latent infection (13). Indeed, in vivo, the anti-monkey $\alpha 4\beta 7$ antibody surprisingly promoted the repopulation of CD4 T cells in a wide variety of immune tissues including gastro-intestinal tissues (GITs) (31), suggesting that in this SIV-infection setting, the anti-$\alpha 4\beta 7$ antibody was not effective in blocking T cell homing, but rather it may have triggered an "outside-in" signal. Such signaling would have synergized with chemotactic signaling in restoring T cell chemotaxis to tissues. Early restoration of CD4 T cells in the gut is associated with immune reconstitution and effective control of viremia without the need for ART (31, 41). The $\alpha 4\beta 7$ receptors are expressed primarily on memory CD4 T cells, and high levels of $\alpha 4\beta 7$ are associated with T cell migration preferentially into mucosal tissues such as GITs (42, 43), in which CD4 T cells are severely depleted during HIV/SIV infection (20, 21). A full CD4 T cell repopulation in the gut is rarely achieved with ART, allowing continuous chronic immune activation (21, 44). Persistent cofilin hyperactivation is likely one of the major reasons for this lack of T cell repopulation in the gut (5). A T cell subpopulation that is key to maintaining mucosal integrity is Th17 cells (45), which are depleted in both HIV infection and pathogenic SIV infection (8, 46, 47). Although ART restores Th17 cells in the bloodstream, it does not lead to full reconstitution of the Th17 cells in the mucosal compartment (9, 10, 47-49). Virologically, the Th17 cells are highly permissive to HIV-1, and this permissiveness is linked to the expression of CCR6, CCR5, CCR9, and $\alpha 4\beta 7$ (47, 50, 51). Recently, it has been shown that the CCR6+ and CCR3+ Th cells are impaired in trafficking from the blood stream to peripheral tissues (5), and these cells are accumulated in the peripheral blood as a predominate viral reservoir (52). Therefore, therapeutically, targeting the cofilin pathway would bring at least two major benefits (FIG. 4G); for uninfected cells, the restoration of cofilin-mediated CD4 T cell homing and repopulation in GALTs and other lymphoid tissues would help immune reconstitution; for infected cells, homing of these latent HIV+ cells to lymphoid tissues may lead to their reactivation and eventual containment by the restored immune system, reducing latent viral reservoirs persisting in the peripheral blood. In sum, the study suggests that cofilin is a key molecule that needs to be therapeutically targeted to achieve a functional cure of HIV infection (FIG. 4G).

Materials and Methods for Examples

Clinical Study.

All clinical study protocols were reviewed and approved by the Ethics Review Committee of China Medical University (CMU), Shenyang, P. R. China, and written informed consent from each participant in the study was obtained. 200 HIV-1 infected patients from the HIV patient cohort of the Key Laboratory of AIDS Immunology of National Health and Family Planning Commission in the First Affiliated Hospital of China Medical University were enrolled. Among the HIV-infected patients, 98 had no previous and current antiretroviral therapy (ART) at the time of the p-cofilin profiling, and 102 had ongoing ART for over a year, but 4 of the ART-treated patients had a viral load greater than 1,000 copies/ml and were excluded from the study for possible drug-resistance. The CD4 T cell count and viral load of these subjects were measured every 3 months. One hundred age- and sex-matched healthy controls (HC) were enrolled from the HIV voluntary counseling and testing center of China Medical University. A summary of the subjects is listed in table S1. For the ART naïve patients, 65 of them eventually received ART at around 6 months after the p-cofilin profiling and were treated for over a year. All of these patients receiving ART reached undetectable plasma HIV-1 RNA. ART-treated patients were further evaluated and categorized into immune responders (IR) and Immune non-responders (INR). Both IR and INR were treated with ART for over one year. IRs were those who had a CD4 T cell recovery greater than 20% and a CD4 T cell count higher than 500 cells/μl; INRs had a CD4 T cell recovery less than 20% or a CD4 T cell count lower than 200 cells/μl.

For isolating blood resting CD4 T cells from study subjects, peripheral blood mononuclear cells were freshly obtained from the subjects, and purified by Ficoll-Hypaque density gradient centrifugation, followed by negative isolation of resting CD4 T cells as previously described (13, 54). Briefly, monoclonal antibodies against human CD14, CD56, HLA-DR, DP, and DQ, CD8, CD11 b and CD19 (BD Biosciences, San Jose, Calif.) were used. Antibody-bound cells were depleted using Dynabeads Pan Mouse IgG (Thermo Fisher Scientific). Purified cells were cultured in RPMI 1640 medium supplemented with 10% FBS.

One million resting CD4 T cells from each blood donor were lysed in 40 μl SDS/T-PER extraction buffer [Novex Tris-Glycine SDS Sample Buffer, T-PER Tissue Protein Extraction Reagent (Thermo Fisher Scientific) and 2.5% 2-mercaptoethanol (Sigma-Aldrich)]. Cell lysates were heated at 100° C. for 8 minutes, immediately freeze and stored at −80° C., and then transported on dry ice to Theranostics Health (Gaithersburg, Md., USA) for cofilin reverse phase protein microarray analyses. A total of 296 coded cell lysates were printed onto the microarrays and profiled, and 3 lysates did not generate readable signals and were excluded from data analyses.

Reverse Phase Protein Microarray (RPPA).

Details of RPPA has been published previous (27, 55). The RPPA directly couples the phospho-cofilin detection antibody with highly sensitive amplification systems that can yield detection sensitivities to fewer than 1,000 to 5,000 molecules per spot with good linearity (correlation coefficient or $R^2$=0.990-0.999) and inter-experiment precision ($R^2$=0.973). Published between run and within run analytical precision in these studies is between a 3-13% CV (coefficient of variation) (55-57). The RPPA technology has been developed and optimized for performance as a fluorescent-based calibrated assay, generally identical in design and analysis to standard ELISA or standard clinical immunoassays. Each array consists of patient cell lysates printed in triplicate two-spot dilutions (neat and 1:4), high, and low controls printed in triplicate two-spot dilutions (neat and 1:4), and 6-10 point calibrators. The analyte concentration is thereby determined by extrapolation to a non-parametrically determined curve fit of the calibration curve and reported in relative fluorescent units.

For Data normalization, each protein analyte value is normalized to the total amount of protein printed on that spot with a florescent stain (Sypro Ruby Blot Stain, Molecular Probes, Eugene Oreg.) that binds to the amne group of proteins without bias. The protein loading value is also obtained by a calibrated assay technique. This total protein calibrator consists of a protein lysate with a known concentration, which upon dilution, spans the linear dynamic range of protein concentration. Each sample value is then extrapolated to the calibrator.

Purification of Resting CD4 T Subtypes from Peripheral Blood.

All protocols involving human subjects were reviewed and approved by the George Mason University institutional review board. Peripheral blood mononuclear cells (PBMC) were purified from peripheral blood of HIV-negative donors by centrifugation in Lymphocyte Separation Medium (Corning, Corning, N.Y.), and resting CD4 T cells were further purified by two rounds of negative selection as previously described (13, 54). Briefly, for the first-round depletion, monoclonal antibodies against human CD14, CD56 and HLA-DR, DP, and DQ (BD Biosciences, San Jose, Calif.) were used. For the second-round depletion, monoclonal antibodies against human CD8, CD11b, and CD19 (BD Biosciences, San Jose, Calif.) were used. Antibody-bound cells were depleted using Dynabeads Pan Mouse IgG (Invitrogen, Carlsbad, Calif.). For further negative selection of the memory and naïve CD4 T cell subsets, monoclonal antibody against either CD45RA (0.02 µl per million cells) or CD45RO (0.1 µl per million cells) (BD Biosciences, San Jose, Calif.) was added during the second round of depletion. Purified cells were cultured in RPMI-1640 medium supplemented with 10% heat-inactivated fetal bovine serum (Invitrogen, Carlsbad, Calif.), penicillin (50 U/ml) (Invitrogen, Carlsbad, Calif.), and streptomycin (50 µg/ml) (Invitrogen, Carlsbad, Calif.). Cells were rested overnight before infection or treatment. For $\alpha 4\beta 7$ surface receptor upregulation, resting CD4 T cells were also cultured in IL-7 (5 ng/ml) for 3 days.

Cell Lines and Viruses.

A3R5.7 cell is acquired from the NIH AIDS Reagent Program. A3R5.7 is derived from A3.01 that naturally expresses CD4, CXCR4, $\alpha 4\beta 7$, and was engineered to express CCR5 (58, 59). HIV-1(AD8) was kindly provided by Dr. Malcolm A. Martin) (60). Virus stocks of NLENG1-ES-IRES(NL4-3), NLENG1-ES-IRES(Yu2), and HIV-1 (AD8) were prepared by transfection of HEK293T cells with cloned proviral DNA as described (13, 54). Viral titer ($TCID_{50}$) was determined on the Rev-dependent GFP indicator cell (61), Rev-A3R5-GFP (Virongy, Manassas, Va.). For viral infection of resting CD4 T cells, cells were infected with envelope-negative GFP reporter HIV-1 virus NLENG1-ES-IRES, pseudo-typed with NL4-3 or YU2 envelope. Infection were performed by spinoculation for 2 hours at 1200×g of 400 virions particles per cell at 37° C., in the presence of 5 ug/ml DEAE Dextran (Sigma). After infection cells were washed and incubated for 6 days with or without IL-7 (R&D Systems, 25 ng/ml). T cells were stained with anti-CD45RO-Pacific Blue monoclonal antibody (BD Pharmingen) and analyzed by Flow Cytometry for CD45RO and GFP expression. For treatment of resting CD4 T cells with HIV(AD8), cells were pretreated with or without pertussis toxin (100 ng/ml) (Sigma) for 1 hour at 37° C., and then treated with HIV(AD8) ($10^{3.5}$ to $10^{4.5}$ $TCID_{50}$ per million cells) for various time. Cells were fixed and stained for intracellular p-cofilin. For treatment of resting CD4 T cells with HIV gp120(BAL) (from the NIH AIDS Reagent Program), cells were treated with or without maravoric (1 µM) (from the NIH AIDS Reagent Program) for 1 hour at 37° C., and then treated with for HIV gp120(BAL) (100 nM) for various time.

Western Blotting for p-Cofilin and Cofilin.

One million cells were lysed in NuPAGE LDS Sample Buffer (Invitrogen, Carlsbad, Calif.) followed by sonication. Samples were heated at 70° C. for 10 minutes, separated by SDS-PAGE, and then transferred onto nitrocellulose membranes (Invitrogen, Carlsbad, Calif.). The membranes were washed in TBST for 3 minutes and then blocked for 30 minutes at room temperature with 5% milk. The blots were incubated with a mouse anti-cofilin antibody (1:1000 dilution) (BD Biosciences, San Jose, Calif.) and a rabbit anti-phospho-cofilin (ser3) antibody (1:500 dilution) (Cell Signaling) diluted in 3% milk-TBST and rocked overnight at 4° C. The blots were washed three times for 15 minutes, then incubated with DyLight 680 goat anti-mouse and DyLight 800 goat anti-rabbit antibodies (KPL, Gaithersburg, Md.) (1:5000 diluted in blocking buffer) for 1 h at 4° C. The blots were washed three times for 15 minutes and scanned with Odyssey Infrared Imager (Li-cor Biosciences).

Intracellular p-Cofilin Staining and Flow Cytometry.

One million cells were fixed, permeabilized with methanol, washed, and then stained with an anti-human p-cofilin antibody using a commercial intracellular staining kit (Virongy, Manassas, Va.) for 60 min at room temperature. Cells were washed twice and stained with Alexa Fluor 488-labeled chicken anti-rabbit antibodies (Invitrogen, Carlsbad, Calif.). Cells were washed twice, and then analyzed on a FACSCalibur (BD Biosciences, San Jose, Calif.).

Surface Staining of CCR5 and $\alpha 4\beta 7$.

Cells were stained with PE-labeled Rat anti-human CCR5 antibody (Biolegend, San Diego, Calif.) or with a mouse anti-human $\alpha 4\beta 7$ integrin antibody (Act-1) (obtained from NIH AIDS Reagent Program) followed by secondary antibody staining with Alexa Fluor 647-labelled goat anti-mouse antibodies (Invitrogen, Carlsbad, Calif.). Cells were stained on ice in PBS+0.1% BSA for 30 minutes, washed with cold PBS-0.5% BSA, and then analyzed on a FACSCalibur (BD Biosciences, San Jose, Calif.).

Chemotaxis Assay.

A half million cells were resuspended into 100 µl RPMI-1640 medium and then added to the upper chamber of a 24-well trans-well plate (Corning, Corning, N.Y.). The lower chamber was filled with 600 µl of medium premixed with SDF-1 (40 ng/ml). The plate was incubated at 37° C. for 2 hours, and then the upper chamber was removed and cells in the lower chamber were counted. Where indicated, different concentrations of R10015 (29) or DMSO were added to cell culture, incubated for 1 hour at 37° C. before adding cells to the upper chamber. Cells were also treated with the anti-human α4β7 integrin antibody (Act-1) or the control mouse IgG1 antibody for 15 minutes before adding cells to the upper chamber. Act-1 (1 µg/ml) was also added to the lower chamber with SDF-1 (40 ng/ml).

Statistical Analysis.

Figure 2:
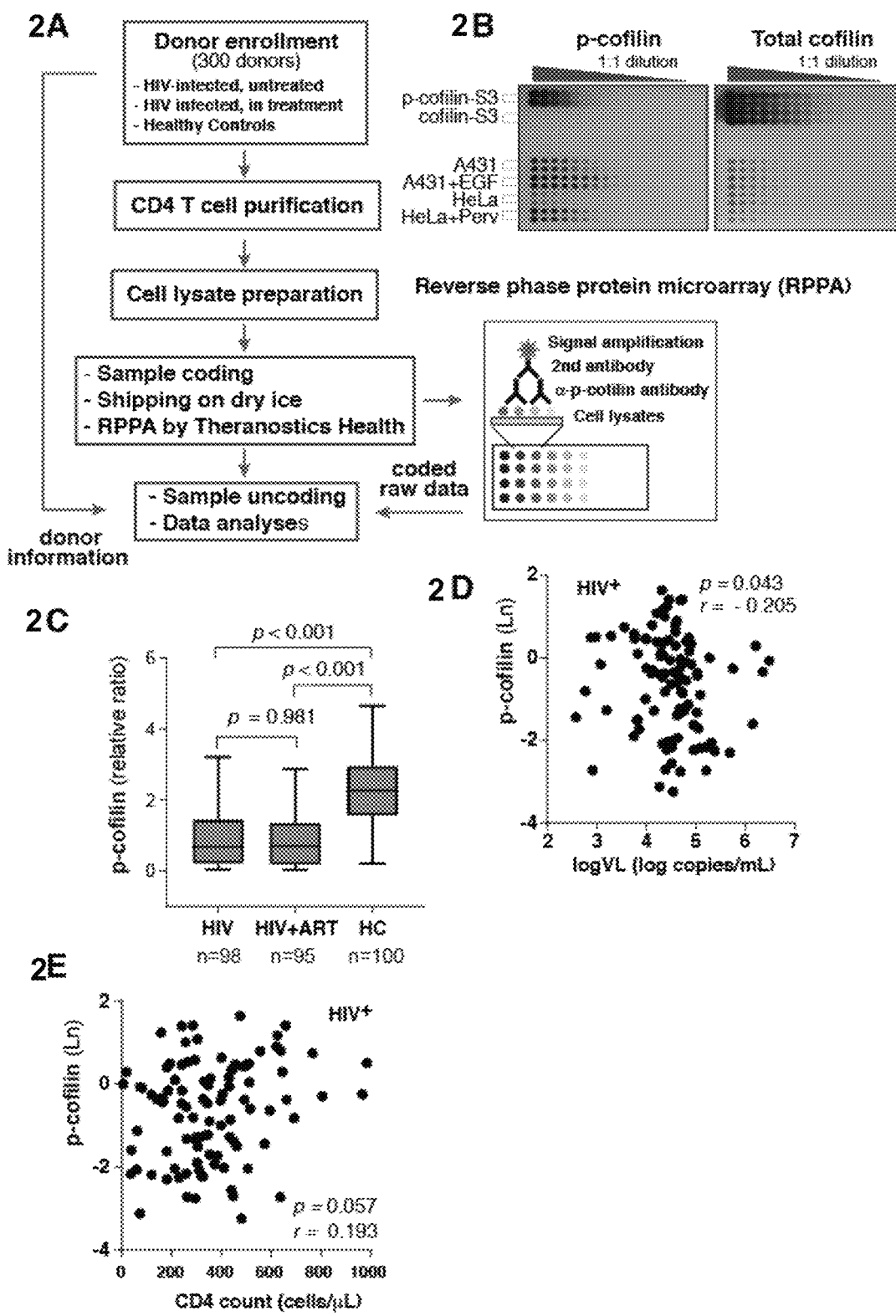
FIGS. 2A-2E show cofilin hyperactivation in HIV infection. (A) Flowchart of the clinical study. (B) Development of the reverse-phase cofilin microarray for profiling cofilin phosphorylation. Synthetic peptides or cell lysates were serially diluted (1:1) and printed onto the microarray slides, which were then stained with antibodies against either total cofilin (right) or phospho-cofilin (left). P-cofilin-S3, a synthetic cofilin peptide with serine 3 phosphorylated; cofilin-S3, a similar peptide with no serine 3 phosphorylation. A431 or HeLa cells were not treated or treated with human epithelial growth factor (EGF) or pervanadate (Perv). (C) Relative levels of p-cofilin in blood resting CD4 T cells from HIV-infected patients with (HIV+ART) or without ART (HIV), or healthy control donors (HC) were profiled. Box plots show interquartile range, median, and range. (D and E) The correlation between levels of p-cofilin and plasma viral load (D) and CD4 T cell count (E) in untreated patients were plotted using Spearman rank correlation tests (Ln, natural logarithm).

Statistical calculations were performed using IBM SPSS statistics 23. Categorical data were described and analyzed by frequency and tchi-square ($\chi 2$) test. For parametric comparison, two-tailed Mann-Whitney U test was used to assess differences between groups during p-cofilin profiling (FIG. 2). Spearman rank correlations tests were used to measure the correlations between variables. Unless otherwise stated, p value less than 0.05 was considered as statistically significant.

CONCLUSION

In a clinical trial, it was found that blood CD4 T cells from HIV-infected patients (n=193), with or without antiretroviral therapy (ART), exhibit significantly higher levels of cofilin dephosphorylation (hyperactivation) than those from healthy controls (n=100) (ratio=1.1/2.3; p<0.001). These results suggest a systemic cofilin-mediated T cell migratory defect that cannot be reversed solely by ART. It was further demonstrated that at low dosages, an anti-human-α4β7 integrin antibody can trigger chemotactic signaling and modulate the cofilin pathway, restoring CD4 T cell motility in vitro. These results suggest that cofilin is a key molecule that needs to be therapeutically targeted for T cell tissue repopulation, immune reconstitution, and immune control of viremia.

All publications, patents and patent applications cited in this specification are incorporated herein by reference in their entireties as if each individual publication, patent or patent application were specifically and individually indicated to be incorporated by reference. While the foregoing has been described in terms of various embodiments, the skilled artisan will appreciate that various modifications, substitutions, omissions, and changes may be made without departing from the spirit thereof.

REFERENCES

1. M. Battegay, R. Nuesch, B. Hirschel, G. R. Kaufmann, Immunological recovery and antiretroviral therapy in HIV-1 infection. *Lancet Infect Dis* 6, 280-287 (2006).
2. M. Clerici et al., Detection of three distinct patterns of T helper cell dysfunction in asymptomatic, human immunodeficiency virus-seropositive patients. Independence of CD4+ cell numbers and clinical staging. *J Clin Invest* 84, 1892-1899 (1989).
3. R. J. Gurley, K. Ikeuchi, R. A. Byrn, K. Anderson, J. E. Groopman, CD4+ lymphocyte function with early human immunodeficiency virus infection. *Proc Natl Acad Sci USA* 86, 1993-1997 (1989).
4. A. M. Masci et al., HIV-1 gp120 induces anergy in naive T lymphocytes through CD4-independent protein kinase-A-mediated signaling. *J Leukoc Biol* 74, 1117-1124 (2003).
5. V. Cecchinato et al., Impairment of CCR6+ and CXCR3+ Th Cell Migration in HIV-1 Infection Is Rescued by Modulating Actin Polymerization. *J Immunol* 198, 184-195 (2017).
6. M. Mavigner et al., Altered CD4+ T cell homing to the gut impairs mucosal immune reconstitution in treated HIV-infected individuals. *J Clin Invest* 122, 62-69 (2012).
7. S. Perez-Patrigeon et al., HIV infection impairs CCR7-dependent T-cell chemotaxis independent of CCR7 expression. *Aids* 23, 1197-1207 (2009).
8. V. Cecchinato et al., Altered balance between Th17 and Th1 cells at mucosal sites predicts AIDS progression in simian immunodeficiency virus-infected macaques. *Mucosal Immunol* 1, 279-288 (2008).
9. G. d'Ettorre et al., Reconstitution of intestinal CD4 and Th17 T cells in antiretroviral therapy suppressed HIV-infected subjects: implication for residual immune activation from the results of a clinical trial. *PLoS One* 9, e109791 (2014).
10. E. S. Ryan et al., Loss of Function of Intestinal IL-17 and IL-22 Producing Cells Contributes to Inflammation and Viral Persistence in SIV-Infected Rhesus Macaques. *PLoS Pathog* 12, e1005412 (2016).
11. Z. Q. Zhang et al., Reversibility of the pathological changes in the follicular dendritic cell network with treatment of HIV-1 infection. *Proc Natl Acad Sci USA* 96, 5169-5172 (1999).
12. D. Finzi et al., Identification of a reservoir for HIV-1 in patients on highly active antiretroviral therapy [see comments]. *Science* 278, 1295-1300 (1997).
13. A. Yoder et al., HIV envelope-CXCR4 signaling activates cofilin to overcome cortical actin restriction in resting CD4 T cells. *Cell* 134, 782-792 (2008).
14. Y. Wu, A. Yoder, Chemokine coreceptor signaling in HIV-1 infection and pathogenesis. *PLoS Pathog* 5, e1000520 (2009).
15. Y. Feng, C. C. Broder, P. E. Kennedy, E. A. Berger, HIV-1 entry cofactor: functional cDNA cloning of a seven-transmembrane, G protein-coupled receptor. *Science* 272, 872-877 (1996).
16. P. U. Cameron et al., Establishment of HIV-1 latency in resting CD4+ T cells depends on chemokine-induced changes in the actin cytoskeleton. *Proc Natl Acad Sci USA* 107, 16934-16939 (2010).
17. P. Lappalainen, D. G. Drubin, Cofilin promotes rapid actin filament turnover in vivo. *Nature* 388, 78-82 (1997).
18. Y. Samstag, S. M. Eibert, M. Klemke, G. H. Wabnitz, Actin cytoskeletal dynamics in T lymphocyte activation and migration. *J Leukoc Biol* 73, 30-48 (2003).
19. Y. Wu et al., Cofilin activation in peripheral CD4 T cells of HIV-1 infected patients: a pilot study. *Retrovirology* 5, 95 (2008).
20. R. S. Veazey et al., Gastrointestinal tract as a major site of CD4+ T cell depletion and viral replication in SIV infection. *Science* 280, 427-431. (1998).
21. J. M. Brenchley et al., Microbial translocation is a cause of systemic immune activation in chronic HIV infection. *Nat Med* 12, 1365-1371 (2006).
22. M. Melar, D. E. Ott, T. J. Hope, Physiological levels of virion-associated human immunodeficiency virus type 1 envelope induce coreceptor-dependent calcium flux. *J Virol* 81, 1773-1785 (2007).
23. B. Ramratnam et al., The decay of the latent reservoir of replication-competent HIV-1 is inversely correlated with the extent of residual viral replication during prolonged anti-retroviral therapy. *Nat Med* 6, 82-85 (2000).
24. B. Ramratnam et al., Intensification of antiretroviral therapy accelerates the decay of the HIV-1 latent reservoir and decreases, but does not eliminate, ongoing virus replication. *J Acquir Immune Defic Syndr* 35, 33-37 (2004).
25. T. Zhu et al., Evidence for human immunodeficiency virus type 1 replication in vivo in CD14(+) monocytes and its potential role as a source of virus in patients on highly active antiretroviral therapy. *J Virol* 76, 707-716 (2002).
26. D. M. Brainard et al., Migration of antigen-specific T cells away from CXCR4-binding human immunodeficiency virus type 1 gp120. *Journal of Virology* 78, 5184-5193 (2004).
27. M. Pierobon, C. Belluco, L. A. Liotta, E. F. Petricoin, 3rd, Reverse phase protein microarrays for clinical applications. *Methods Mol Biol* 785, 3-12 (2011).
28. N. Yang et al., Cofilin phosphorylation by LIM-kinase 1 and its role in Rac-mediated actin reorganization. *Nature* 393, 809-812 (1998).
29. F. Yi et al., Discovery of Novel Small Molecule Inhibitors of LIM Domain Kinase for Inhibiting HIV-1. *J Virol*, (2017).
30. P. J. Vorster et al., LIM kinase 1 modulates cortical actin and CXCR4 cycling and is activated by HIV-1 to initiate viral infection. *J Biol Chem* 286, 12554-12564 (2011).
31. S. N. Byrareddy et al., Sustained virologic control in SIV+ macaques after antiretroviral and alpha4beta7 antibody therapy. *Science* 354, 197-202 (2016).
32. C. C. Denucci, J. S. Mitchell, Y. Shimizu, Integrin function in T-cell homing to lymphoid and nonlymphoid sites: getting there and staying there. *Crit Rev Immunol* 29, 87-109 (2009).
33. B. Shen, M. K. Delaney, X. Du, Inside-out, outside-in, and inside-outside-in: G protein signaling in integrin-mediated cell adhesion, spreading, and retraction. *Curr Opin Cell Biol* 24, 600-606 (2012).
34. C. Kim, F. Ye, M. H. Ginsberg, Regulation of integrin activation. *Annu Rev Cell Dev Biol* 27, 321-345 (2011).
35. T. Kinashi, Intracellular signalling controlling integrin activation in lymphocytes. *Nat Rev Immunol* 5, 546-559 (2005).
36. R. Cimbro et al., IL-7 induces expression and activation of integrin alpha4beta7 promoting naive T-cell homing to the intestinal mucosa. *Blood* 120, 2610-2619 (2012).
37. R. F. Bargatze, E. C. Butcher, Rapid G protein-regulated activation event involved in lymphocyte binding to high endothelial venules. *J Exp Med* 178, 367-372 (1993).
38. K. H. Lee, S. C. Meuer, Y. Samstag, Cofilin: a missing link between T cell co-stimulation and rearrangement of the actin cytoskeleton. *Eur J Immunol* 30, 892-899 (2000).
39. S. M. Eibert et al., Cofilin peptide homologs interfere with immunological synapse formation and T cell activation. *Proc Natl Acad Sci USA* 101, 1957-1962 (2004).
40. M. Schweneker, D. Favre, J. N. Martin, S. G. Deeks, J. M. McCune, HIV-induced changes in T cell signaling pathways. *J Immunol* 180, 6490-6500 (2008).
41. B. Ling et al., Early restoration of mucosal CD4 memory CCR5 T cells in the gut of SIV-infected rhesus predicts long term non-progression. *Aids* 21, 2377-2385 (2007).
42. M. Kader et al., Alpha4(+)beta7(hi)CD4(+) memory T cells harbor most Th-17 cells and are preferentially infected during acute SIV infection. *Mucosal Immunol* 2, 439-449 (2009).
43. W. W. Agace, Tissue-tropic effector T cells: generation and targeting opportunities. *Nat Rev Immunol* 6, 682-692 (2006).
44. S. G. Deeks et al., Immune activation set point during early HIV infection predicts subsequent CD4+ T-cell changes independent of viral load. *Blood* 104, 942-947 (2004).
45. T. Korn, E. Bettelli, M. Oukka, V. K. Kuchroo, IL-17 and Th17 Cells. *Annu Rev Immunol* 27, 485-517 (2009).
46. J. M. Brenchley et al., Differential Th17 CD4 T-cell depletion in pathogenic and nonpathogenic lentiviral infections. *Blood* 112, 2826-2835 (2008).
47. Y. Alvarez et al., Preferential HIV infection of CCR6+ Th17 cells is associated with higher levels of virus receptor expression and lack of CCR5 ligands. *J Virol* 87, 10843-10854 (2013).
48. A. El Hed et al., Susceptibility of human Th17 cells to human immunodeficiency virus and their perturbation during infection. *J Infect Dis* 201, 843-854 (2010).
49. M. Macal et al., Effective CD4+ T-cell restoration in gut-associated lymphoid tissue of HIV-infected patients is associated with enhanced Th17 cells and polyfunctional HIV-specific T-cell responses. *Mucosal Immunol*, 475-488 (2008).
50. A. Gosselin et al., Peripheral blood CCR4+CCR6+ and CXCR3+CCR6+CD4+ T cells are highly permissive to HIV-1 infection. *J Immunol* 184, 1604-1616 (2011).
51. P. Monteiro et al., Memory CCR6+CD4+ T cells are preferential targets for productive HIV type 1 infection regardless of their expression of integrin beta7. *J Immunol* 186, 4618-4630 (2011).
52. G. Khoury et al., Persistence of integrated HIV DNA in CXCR3+CCR6+ memory CD4+ T cells in HIV-infected individuals on antiretroviral therapy. *AIDS* 30, 1511-1520 (2016).
53. M. Spear, J. Guo, Y. Wu, Novel anti-HIV therapeutics targeting chemokine receptors and actin regulatory pathways. *Immunological Reviews* DOI: 10.111/imr.12106, (2013).
54. Y. Wu, J. W. Marsh, Selective transcription and modulation of resting T cell activity by preintegrated HIV DNA. *Science* 293, 1503-1506. (2001).
55. C. P. Paweletz et al., Reverse phase protein microarrays which capture disease progression show activation of pro-survival pathways at the cancer invasion front. *Oncogene* 20, 1981-1989 (2001).
56. A. J. VanMeter et al., Laser capture microdissection and protein microarray analysis of human non-small cell lung cancer: differential epidermal growth factor receptor (EGPR) phosphorylation events associated with mutated EGFR compared with wild type. *Mol Cell Proteomics* 7, 1902-1924 (2008).
57. J. D. Wulfkuhle et al., Molecular analysis of HER2 signaling in human breast cancer by functional protein pathway activation mapping. *Clin Cancer Res* 18, 6426-6435 (2012).
58. R. J. McLinden et al., Detection of HIV-1 neutralizing antibodies in a human CD4(+)/CXCR4(+)/CCR5(+) T-lymphoblastoid cell assay system. *PLoS One* 8, e77756 (2013).
59. T. Folks et al., Characterization of a continuous T-cell line susceptible to the cytopathic effects of the acquired immunodeficiency syndrome (AIDS)-associated retrovirus. *Proc Natl Acad Sci USA* 82, 4539-4543 (1985).
60. G. Englund, T. S. Theodore, E. O. Freed, A. Engleman, M. A. Martin, Integration is required for productive infection of monocyte-derived macrophages by human immunodeficiency virus type 1. *J Virol* 69, 3216-3219 (1995).
61. Y. Wu, M. H. Beddall, J. W. Marsh, Rev-dependent indicator T cell line. *Current HIV Research* 5, 395-403 (2007).

The invention claimed is:
1. A method comprising: identifying cofilin hyperactivation by obtaining or having obtained a biological sample from a patient and performing or having performed an assay on the biological sample to profile cofilin phosphorylation;

identifying loss of chemotaxis of T-cells in the biological sample;

obtaining an agent comprising an anti-α4β7 integrin antibody and a chemokine comprising stromal cell-derived factor 1 (SDF-1), and administering the agent in the patient.

2. The method of claim 1, wherein the method is for treating a subject infected with HIV.

3. The method of claim 1, wherein the anti-α4β7 integrin antibody is administered about 0.1 mg to about 500 mg per kg body weight of the patient.

4. The method of claim 1, wherein the anti-α4β7 integrin antibody is a human anti-α4β7 integrin antibody or a humanized anti-α4β7 integrin antibody.

5. The method of claim 1, wherein one or more T cell functions lost to the cofilin hyperactivation are T cell motility, T cell migration and homing to lymphoid and non-lymphoid tissues, T cell tissue repopulation, and/or CD4 T cell repopulation.

6. The method of claim 1, wherein the method further comprises treating the patient prior to, subsequent to, or at the same time with antiretroviral therapy (ART).

7. The method of claim 1, wherein the anti-α4β7 integrin antibody configured to stimulate a chemokine receptor or an integrin receptor comprises an anti-CXCR4, an anti-CCR5, or an Act-1.

8. The method of claim 5, wherein the administering the agent is configured to restores one or more T cell functions or reverses hyperactivation of cofilin in cells of the patient.

9. The method of claim 1, wherein the agent enhances or decreases cofilin phosphorylation and/or enhances actin polymerization or actin depolymerization.

10. The method of claim 1, wherein the agent is configured to restore T-cell chemotaxis, immune reconstitution, immune control of viremia, and/or one or more T cell functions lost due to cofilin hyperactivation in the patient.

11. A method comprising: identifying cofilin hyperactivation by obtaining or having obtained a biological sample from a patient and performing or having performed an assay on the biological sample to profile cofilin phosphorylation; identifying loss of chemotaxis of T-cells in the biological sample; obtaining an agent comprising an anti-α4β7 integrin antibody and a chemokine comprising a molecule having an ability to bind at a chemokine receptor comprising CCR5 and/or CXCR4 and a chemotactic property, and administering the agent in the patient.

12. The method of claim 11, wherein the agent is configured to restores T-cell chemotaxis, immune reconstitution, immune control of viremia, and/or one or more T cell functions lost due to cofilin hyperactivation in the patient.

13. The method of claim 11, wherein the method is for treating a subject infected with HIV.

14. The method of claim 11, wherein the anti-α4β7 integrin antibody configured to stimulate the chemokine receptor or an integrin receptor comprises an anti-CXCR4, an anti-CCR5, or an Act-1.

15. The method of claim 11, wherein the administering the agent is configured to restores one or more T cell functions or reverses hyperactivation of cofilin in cells of the patient.

16. The method of claim 11, wherein the agent enhances or decreases cofilin phosphorylation and/or enhances actin polymerization or actin depolymerization.

17. A method comprising: identifying cofilin hyperactivation by obtaining or having obtained a biological sample from a patient and performing or having performed an assay on the biological sample to profile cofilin phosphorylation; identifying loss of chemotaxis of T-cells in the biological sample; obtaining an agent comprising an anti-α4β7 integrin antibody and a chemokine comprising a molecule having a chemotactic property of stromal cell-derived factor 1 (SDF-1), and administering the agent in the patient.

18. The method of claim 17, wherein the agent is configured to restores T-cell chemotaxis, immune reconstitution, immune control of viremia, and/or one or more T cell functions lost due to cofilin hyperactivation in the patient.

19. The method of claim 17, wherein the method is for treating a subject infected with HIV.

* * * * *